(12) United States Patent
Oniciu

(10) Patent No.: US 11,566,005 B2
(45) Date of Patent: Jan. 31, 2023

(54) HIGHLY PURE PHENTOLAMINE MESYLATE AND METHODS FOR MAKING SAME

(71) Applicant: Ocuphire Pharma, Inc., Farmington Hills, MI (US)

(72) Inventor: Daniela Carmen Oniciu, Gainesville, FL (US)

(73) Assignee: Ocuphire Pharma, Inc., Farmington Hills, MI (US)

( * ) Notice: Subject to any disclaimer, the term of this patent is extended or adjusted under 35 U.S.C. 154(b) by 0 days.

(21) Appl. No.: 17/747,656

(22) Filed: May 18, 2022

(65) Prior Publication Data

US 2022/0388965 A1    Dec. 8, 2022

Related U.S. Application Data

(60) Provisional application No. 63/189,839, filed on May 18, 2021.

(30) Foreign Application Priority Data

Jun. 18, 2021    (CN) .......................... 202110679032.9

(51) Int. Cl.
*C07D 233/24*    (2006.01)

(52) U.S. Cl.
CPC .................. *C07D 233/24* (2013.01)

(58) Field of Classification Search
CPC .................................................... C07D 233/24
See application file for complete search history.

(56) References Cited

U.S. PATENT DOCUMENTS

| | | |
|---|---|---|
| 4,252,721 A | 2/1981 | Silvestrini et al. |
| 4,443,441 A | 4/1984 | Galin |
| 4,508,715 A | 4/1985 | Booth et al. |
| 4,515,295 A | 5/1985 | Dougherty |
| 4,590,202 A | 5/1986 | Remy |
| 4,629,456 A | 12/1986 | Edwards |
| 4,659,714 A | 4/1987 | Watt-Smith |
| 4,834,727 A | 5/1989 | Cope |
| 4,888,344 A | 12/1989 | Sunagawa et al. |
| 4,906,613 A | 3/1990 | Watkins |
| 4,938,970 A | 7/1990 | Hustead et al. |
| 5,032,392 A | 7/1991 | Varma |
| 5,059,188 A | 10/1991 | Goddard |
| 5,134,124 A | 7/1992 | Nisato et al. |
| 5,149,320 A | 9/1992 | Dhaliwal et al. |
| 5,192,527 A | 3/1993 | Abrahmsohn |
| 5,261,903 A | 11/1993 | Dhaliwal et al. |
| 5,281,591 A | 1/1994 | Burke |
| 5,288,759 A | 2/1994 | DeSantis, Jr. |
| 5,488,050 A | 1/1996 | Neufeld |
| 5,514,118 A | 5/1996 | Kummer et al. |
| 5,584,823 A | 12/1996 | Valberg |
| 5,591,426 A | 1/1997 | Dabrowski et al. |
| 5,627,611 A | 5/1997 | Scheiner |
| 5,792,767 A | 8/1998 | Meyer et al. |
| 5,885,550 A | 3/1999 | Vallier |
| 5,891,882 A | 4/1999 | Meyer et al. |
| 5,891,913 A | 4/1999 | Sallmann et al. |
| 5,895,654 A | 4/1999 | Hartford et al. |
| 6,001,845 A | 12/1999 | Estok |
| 6,025,396 A | 2/2000 | Kim et al. |
| 6,043,224 A | 3/2000 | Lee et al. |
| 6,046,207 A | 4/2000 | Meyer et al. |
| 6,051,594 A | 4/2000 | Lowrey |
| 6,106,866 A | 8/2000 | Ranney |
| 6,291,498 B1 | 9/2001 | Horn |
| 6,420,407 B1 | 7/2002 | Horn |
| 6,432,401 B2 | 8/2002 | Weber et al. |
| 6,469,065 B1 | 10/2002 | Garvey et al. |
| 6,515,006 B2 | 2/2003 | Horn |
| 6,638,537 B2 | 10/2003 | Dennis et al. |
| 6,730,065 B1 | 5/2004 | Horn |
| 6,730,691 B1 | 5/2004 | Galin |
| 6,764,678 B2 | 7/2004 | Weber et al. |
| 6,872,390 B2 | 3/2005 | Weber et al. |
| 7,229,630 B2 | 6/2007 | Chen et al. |
| 7,569,230 B2 | 8/2009 | Chen et al. |
| 7,575,757 B2 | 8/2009 | Chen et al. |
| 7,868,035 B2 | 1/2011 | Woodward et al. |
| 8,299,079 B2 | 10/2012 | Kaufman |
| 8,445,526 B2 | 5/2013 | Horn |
| 8,580,787 B2 | 11/2013 | Horn |
| 8,597,629 B1 | 12/2013 | Horn |

(Continued)

FOREIGN PATENT DOCUMENTS

| | | |
|---|---|---|
| CN | 101402579 A | 4/2009 |
| CN | 101463009 A | 6/2009 |

(Continued)

OTHER PUBLICATIONS

PubChem CID 91430 (create date: Mar. 27, 2005).*

(Continued)

*Primary Examiner* — Deepak R Rao
(74) *Attorney, Agent, or Firm* — Cooley LLP

(57) ABSTRACT

This invention provides methods for synthesizing phentolamine mesylate from phentolamine and methanesulfonic acid in the presence of acetone and water. The methods of the present invention provide highly pure phentolamine mesylate. The invention also provides highly pure phentolamine mesylate.

21 Claims, 4 Drawing Sheets

(56) References Cited

U.S. PATENT DOCUMENTS

| | | |
|---|---|---|
| 8,889,112 B2 | 11/2014 | Horn |
| 8,979,809 B2 | 3/2015 | Horn |
| 9,066,856 B2 | 6/2015 | Demopulos et al. |
| 9,089,560 B2 | 7/2015 | Meyer |
| 9,789,088 B2 | 10/2017 | Meyer |
| 9,795,560 B2 | 10/2017 | Meyer |
| 9,968,594 B2 | 5/2018 | Horn et al. |
| 10,064,818 B2 | 9/2018 | Horn et al. |
| 10,278,918 B2 | 5/2019 | Meyer |
| 10,507,245 B2 | 12/2019 | Vejarano Restrepo |
| 10,610,518 B2 | 4/2020 | Robinson et al. |
| 10,639,297 B2 | 5/2020 | Feinbaum et al. |
| 10,772,829 B2 | 9/2020 | Meyer |
| 10,993,932 B2 | 5/2021 | Pitlick et al. |
| 11,000,509 B2 | 5/2021 | Meyer |
| 11,090,261 B2 | 8/2021 | Meyer |
| 11,400,077 B2 | 8/2022 | Pitlick et al. |
| 2002/0082288 A1 | 6/2002 | Horn |
| 2002/0183356 A1 | 12/2002 | Weber et al. |
| 2002/0183396 A1 | 12/2002 | Weber et al. |
| 2002/0187986 A1 | 12/2002 | Horn |
| 2003/0236306 A1 | 12/2003 | Chen et al. |
| 2004/0053894 A1 | 3/2004 | Mazess et al. |
| 2004/0176408 A1 | 9/2004 | Horn |
| 2005/0080056 A1 | 4/2005 | Horn |
| 2005/0203099 A1 | 9/2005 | Chen et al. |
| 2006/0211753 A1 | 9/2006 | Horn |
| 2006/0257388 A1 | 11/2006 | Knowles |
| 2007/0098748 A1 | 5/2007 | Chen et al. |
| 2008/0020076 A1 | 1/2008 | Jhamandas et al. |
| 2008/0039507 A1 | 2/2008 | Woodward et al. |
| 2009/0131303 A1 | 5/2009 | Hong et al. |
| 2009/0220618 A1 | 9/2009 | Xia et al. |
| 2009/0232763 A1 | 9/2009 | Kabra et al. |
| 2010/0029663 A1 | 2/2010 | Horn |
| 2010/0324031 A1 | 12/2010 | Kabra |
| 2011/0152274 A1 | 6/2011 | Kaufman |
| 2011/0178147 A1 | 7/2011 | Likitlersuang et al. |
| 2012/0136072 A1 | 5/2012 | Mosher et al. |
| 2012/0149748 A1 | 6/2012 | Shanler et al. |
| 2012/0208858 A1 | 8/2012 | Shanler et al. |
| 2012/0238615 A1 | 9/2012 | Chow et al. |
| 2012/0277239 A1 | 11/2012 | Horn et al. |
| 2013/0029919 A1 | 1/2013 | Gore et al. |
| 2013/0143938 A1 | 6/2013 | Horn |
| 2013/0172357 A1 | 7/2013 | Horn |
| 2014/0221445 A1 | 8/2014 | Meyer |
| 2014/0221446 A1 | 8/2014 | Meyer |
| 2015/0150848 A1 | 6/2015 | Horn |
| 2016/0008278 A1 | 1/2016 | Horn et al. |
| 2016/0008337 A1 | 1/2016 | Horn et al. |
| 2016/0051515 A1 | 2/2016 | Meyer |
| 2017/0029365 A1 | 2/2017 | Giordano et al. |
| 2017/0065664 A1 | 3/2017 | Russ |
| 2017/0137453 A1 | 5/2017 | Albrecht et al. |
| 2018/0221274 A1 | 8/2018 | Meyer |
| 2018/0221340 A1 | 8/2018 | Meyer |
| 2019/0248760 A1 | 8/2019 | Liu et al. |
| 2019/0254963 A1 | 8/2019 | Meyer |
| 2019/0321337 A1 | 10/2019 | Robinson et al. |
| 2019/0358152 A1 | 11/2019 | Meyer |
| 2020/0246310 A1 | 8/2020 | Pitlick et al. |
| 2020/0253931 A1 | 8/2020 | Pitlick et al. |
| 2021/0338638 A1 | 11/2021 | Meyer |
| 2021/0346349 A1 | 11/2021 | Pitlick et al. |
| 2022/0175668 A1 | 6/2022 | Meyer |

FOREIGN PATENT DOCUMENTS

| | | |
|---|---|---|
| CN | 102813631 A | 12/2012 |
| CN | 103408495 A | 11/2013 |
| WO | WO-9505188 A1 | 2/1995 |
| WO | WO-9907353 A1 | 2/1999 |
| WO | WO-0119364 A1 | 3/2001 |
| WO | WO-0185171 A1 | 11/2001 |
| WO | WO 03/013515 A1 | 2/2003 |
| WO | WO 2004/000219 A2 | 12/2003 |
| WO | WO-2005123093 A2 | 12/2005 |
| WO | WO-2007008666 A2 | 1/2007 |
| WO | WO-2009077736 A2 | 6/2009 |
| WO | WO-2010135731 A1 | 11/2010 |
| WO | WO-2011050018 A1 | 4/2011 |
| WO | WO-2011050030 A1 | 4/2011 |
| WO | WO-2012075319 A2 | 6/2012 |
| WO | WO-2012112566 A1 | 8/2012 |
| WO | WO-2012119059 A1 | 9/2012 |
| WO | WO-2012119070 A2 | 9/2012 |
| WO | WO-2013115844 A1 | 8/2013 |
| WO | WO-2013130577 A2 | 9/2013 |
| WO | WO-2014121027 A1 | 8/2014 |
| WO | WO-2014121028 A1 | 8/2014 |
| WO | WO-2018033792 A2 | 2/2018 |

OTHER PUBLICATIONS

PubChem CID 517293 (create date: Mar. 27, 2005).*
Machine translation of CN 101463009 published Jun. 24, 2009.*
Jin et al., "Degradation Characteristics of a Novel PAF Receptor Antagonist, SY0916, in Aqueous Solution", Journal of Analytical Methods in Chemistry, 2019, vol. 2019, 8 pages.
Lai Y.Q., Zhang, M.L. and Zhao, B.S. "Improved Synthesis of Phentolamine Mesilate", Huagong Shikan, 2001, vol. 15, No. 5, p. 45-47 (Abstract).
Septodont, Inc, "OraVerse™ (phentolamine mesylate) Injection" Highlights of Prescribing Information, (https://oraverse.com/), Revised, Mar. 2016, 2 pages.
CAS No. 65-28-1 "Phentolamine Mesylate", MOLBASE, Last Updated: Oct. 31, 2016, 2 pages.
Abad et al., "Comparison of Astigmatism Correction Using Shorter Arc Length 90° /120° Asymmetric Intacs Severe Keratoconus Versus 150° Single-Segment Intacs Severe Keratoconus in Asymmetric Keratoconus," Cornea, (2011), vol. 30, No. 11, pp. 1201-1206.
Abdelkader, A., & Kaufman, H. E. (2016). Clinical outcomes of combined versus separate carbachol and brimonidine drops in correcting presbyopia. Eye and Vision, 3(1), 31.
Abelson, et al., A. "The Truth about Tachyphylaxis", Review of Ophthalmology, (2006), vol. 13, No. 3, p. 112-115.
ACETADOTE® (acetylcysteine) Prescribing Information/ Package Insert / Label, Approval 2004, Revised 2008, Manufactured for Cumberland Pharmaceuticals Inc., Nashville, TN, 7 pages.
Ackerman, S. L., Torkildsen, G. L., Mclaurin, E., & Vittitow, J. L. (2019). Low-dose brimonidine for relief of ocular redness: Integrated analysis of four clinical trials. Clinical and Experimental Optometry, 102(2), 131-139.
ACULAR® Prescribing Information/ Package Insert / Label, 2012, Allergan, Inc., Palo Alto, CA, USA, Reference ID: 72379US10, 6 pages.
Akutsu, H et al. Contrast Sensitivity and Reading Through Multifocal Intraocular Lenses. Arch Ophthalmol 1992;110:1076-1080.
Alio, J. L., & Azar, D. T. eds. "Management of Complications in Refractive Surgery" 2nd Edition, 2018, Springer, 415 pages.
Al-Khersan H, Flynn H, Townshend J. (2022). Retinal Detachments Associated With Topical Pilocarpine Use for Presbyopia, Am J Ophthalmol., vol. 242, p. 52-55.
Amarikwa L, Michalak SM, Caul S, Mruthyunjaya P, Rahimy E. Vitreofoveal Traction Associated With Pilocarpine for Presbyopia. Ophthalmic Surg Lasers Imaging Retina. Jul. 2022;53(7):410-411.
American Optometric Association. (2020) "Adult Vision: 41 to 60 Years of Age", 5 pages. Retrieved online: https://www.aoa.org/patients-and-public/good-vision-throughout-life/adult-vision-19-to-40-years-of-age/adult-vision-41-to-60-years-of-age.
American Society of Health System Pharmacists; AHFS Drug Information 2010. Bethesda, MD. (2010), p. 1386.
Anastasi, L. M. et al., "Effect of Pilocarpine in Counteracting Mydriasis," Arch. Ophthal., vol. 79, pp. 710-715 (1968).
Antonelli-Lncalzi, R., & Pedone, C. (2007) "Respiratory effects of beta-adrenergic receptor blockers", CurrMed Chem, 14(10), 1121-1128.

(56) References Cited

OTHER PUBLICATIONS

Applegate RA et al. "Metrics of retinal image quality predict visual performance in eyes with 20/17 or better visual acuity", Optom Vis Sci. Sep. 2006; 83(9) 635-640.

ASA, "K-max Plus", Technical Attributes and Typical Analysis, retrieved from http://califasainc.com/pdf/Kmax_Analysis.pdf on May 29, 2016, 1 page.

Barbee and Smith "A Comparative Study of Mydriatic and Cycloplegic Agents: in Human Subjects Without Eye Disease," Am. J. Ophthalmol., vol. 44, No. 5 Pt. 1, p. 617-622 (1957).

Batawi, H. and Micieli, J. A. "Adie's tonic pupil presenting with unilateral photophobia successfully treated with dilute pilocarpine," BMJ Case Rep (2020) 13:e233136.

Bellucci R, et al. "Visual acuity and contrast sensitivity comparison between Tecnis and Acrysof AS60 AT intraocular lenses", J Cataract Refract Surg. 2005; 31:712-717.

Benson et al., "Is Phentolamine Stable in Solution with Papaverine," The Journal of Urology, (1988), vol. 140, p. 970-971.

Besada, E., Reed, K., Najman, P., Shechtman, D., & Hardigan, P. (2011). "Pupillometry Study of Brimonidine Tartrate 0.2% and Apraclonidine 0.5%", The Journal of Clinical Pharmacology, 51(12), p. 1690-1695.

BETAGAN® Prescribing Information / Package Insert / Label, NDA 19219/S-029, Revised Nov. 2017, Allergan, Inc., Palo Alto, CA, USA, Reference ID: 4198172, 8 pages.

Betoptic (Betaxol Hydrochloride Ophthalmic Solution), Pilo PI 2006, Prescribing Information / Package Insert / Label, NDA 19-270/S-031,5 pages.

Bidgoli, S., & Alio, J. L. (2018) "Night Vision Disturbances Following Refractive Surgery: Causes, Prevention, and Treatment", Management of Complications in Refractive Surgery, p. 163-174.

BJO (2017). British Journal of Ophthalmology. European Glaucoma Society Terminology and Guidelines for Glaucoma, 4th Edition—Chapter 3: Treatment Principles and Options. Br J Ophthalmol. 101(6):130-195.[No. authors listed].

Boger, W. P., Steinert, R. F., Puliafito, C. A., & Pavan-Langston, D. (1978). Clinical Trial Comparing Timolol Ophthalmic Solution to Pilocarpine in Open-Angle Glaucoma. American Journal of Ophthalmology, 86(1), 8-18. https://doi.org/10.1016/0002-9394(78)90006-5.

Boland, M. V., Chang, D. S., Frazier, T., Plyler, R., & Friedman, D. S. (2014). "Electronic monitoring to assess adherence with once-daily glaucoma medications and risk factors for nonadherence: the automated dosing reminder study" JAMA Ophthalmol, 132(7), 838-844.

Boyer, D., Patel, R., Khatri, A., et al. (2022). "Phentolamine Ophthalmic Solution Rapidly Reverses Pharmacologically Induced Mydriasis in Two Pivotal Phase 3 MIRA Trials", ASRS Annual Meeting, Abstract ID 665511, 10 pages.

Bradley, A.E., Wancket, L.M., Rinke, M., Gruebbel, M.M., Saladino, B.H., Schafer, K., Katsuta, O., et al. (2021) "International Harmonization of Nomenclature and Diagnostic Criteria (INHAND): Nonproliferative and Proliferative Lesions of the Rabbit", Journal of Toxicologic Pathology, 34 (3_Suppl. 2021-1001), 183S-292S.

Brooks, N. O., Greenstein, S., Fry, K., & Hersh, P. S. (2012). "Patient subjective visual function after corneal collagen crosslinking for keratoconus and corneal ectasia", J Cataract Refract Surg, 38(4), 615-619.

Bruner, R. H., Novilla, M. N., Picut, C. A., Kirkpatrick, J. B., O'Neill, T. P., Scully, K. L., Parker, G. A. (2009). "Spontaneous hibernomas in Sprague-Dawley rats", Toxicol Pathol, 37(4), 547-552.

Brunton L, Chabner B, Knollman. Goodman & Gilman's Pharmacological Basis of Therapeutics, 12th Edition. McGraw-Hill Education/Medical. 2011, p. 308-310.

Büscher R, Heeks C, Taguchi K, Michel MC. Comparison of guinea-pig, bovine and rat alpha 1-adrenoceptor subtypes. Br J Pharmacol. 1996;117(4):703-711.

Cankurtaran, V., & Tekin, K. (2021). "Effects of a Single Dose of Topical Brimonidine 0.15% on Anterior Segment Morphology, Pupil Characteristics, and Choroidal Thickness in Healthy Subjects", Eye & Contact Lens: Science & Clinical Practice, 47(6), 323-329.

Canovetti, A., Nardi, M., Figus, M., Fogagnolo, P., & Benelli, U. (2009). "Aceclidine, brimonidine tartrate, and dapiprazole: Comparison of miotic effect and tolerability under different lighting conditions", Journal of Cataract and Refractive Surgery, 35(1), 42-46.

CDRH/FDA, Summary of Safety and Effectiveness of VISX Star Excimer Laser System, Premarket Approval Application No. P930016/S025, 2007, 9 pages.

Chu, Y.R., Kolli, A., Patel, R., et al. (2022). "The Safety of Phentolamine Ophthalmic Solution for Reversal of Pharmacologically Induced Mydriasis from Multiple Late-Stage Clinical Trials", ASCRS Annual Meeting, Paper ID 80618, 10 pages.

Chylak LT, et al. "Loss of contrast sensitivity in diabetic patients with LOCSII classified cataracts", Brit J Ophthalmol. 1993; 77:78-11.

CLARINEX® (desloratadine) Prescribing Information/ Package Insert/Label, Initial US Approval 2001, Revised Nov. 2015, Manufactured by Bayer, Inc. 10 pages.

Cohen, D. N. and Zakov, A. N. "The Diagnosis of Adie's Pupil Using 0.0625% Pilocarpine Solution," Am. J. Ophthalmol., vol. 79, No. 5, p. 883 (1975).

Csaky KG, Richman EA, Ferris FL. "Report from the NEI/FDA ophthalmic clinical trial design and endpoints symposium", Invest Ophth Vis Sci. Feb. 2008; 49(2) 479-489.

Dart, R.C. (ed). Medical Toxicology. Third Edition, Lippincott Williams & Wilkins. Philadelphia, PA. 2004., Chapter 124 Rauwolfia Alkaloids and Chapter 125 Vasolidators, p. 711-722.

Deeb, S. E., Schepers, U., & Watzig, H. (2006). "Evaluation of monolithic C18 HPLC columns for the fast analysis of pilocarpine hydrochloride in the presence of its degradation products" Die Pharmazie, 9, 751-756.

DeGraff AC, Frieden J, Gould L, Ramana Reddy CV. "Phentolamine", American Heart J (1976) 92:397-402.

Devries, D., Pepose, J., Kolli, A., et al. (2022). "Phentolamine Ophthalmic Solution Reverses Pharmacologically Induced Mydriasis in Healthy Subjects: Subgroup Analyses in the Pivotal Phase 3 MIRA-2 Randomized Placebo Controlled Trial", ARVO Annual Meeting, Abstract ID 3709630, 1 page.

Dexl, A. K., Seyeddain, O., Riha, W., Hohensinn, M., Hitzl, W., & Grabner, G. (2011). "Reading performance after implantation of a small-aperture corneal inlay for the surgical correction of presbyopia: Two-year follow-up", J Cataract Refract Surg, 37(3), 525-531.

Dick HB, et al. "Contrast sensitivity after implantation of toric iris-claw lenses in phakic eyes", J Cataract Refract Surg. 2004; 30:2284-2289.

Diestelhorst, M., Nordmann, J.-P., & Toris, C. B. (2002). "Combined Therapy of Pilocarpine or Latanoprost with Timolol Versus Latanoprost Monotherapy", Survey of Ophthalmology, 47, S155-S161.

Dinsmore WW and Alderdice DK. "Vasoactive intestinal polypeptide and phentolamine mesylate administered by autoinjector in the treatment of patients with erectile dysfunction resistant to other intracavernosal agents" Brit J Urology. 1988; 81:437-440.

D-mannitol Safety Data Sheet by CCI (year 2012), Generic Names: Mannite; Manufacturer: Columbus Chemical Industries, Inc., 65 pages.

Doughty, M. J. and Lyle, W. M. "A Review of the Clinical Pharmacokinetics of Pilocarpine, Moxisylyte (Thymoxamine), and Dapiprazole in the Reversal of Diagnostic Pupillary Dilation," Optometry & Vision Science, vol. 69, No. 5, pp. 358-368 (1992).

Dragoi, V. (2020). "Ocular Motor System", In: Neuroscience Online: An Electronic Textbook for the Neurosciences. The University of Texas Health Science Center at Houston, 15 pages.

Draize, JH. "Appraisal of the Safety of Chemicals in Foods, Drugs and Cosmetics", The Association of Food and Drug Officials of the United States; 1955:49-51.

Draize, J.H., G. Woodward and H.O. Calvery. "Methods for the study of irritation and toxicity of substances applied topically to the skin and mucous membranes", J Pharmacol Exp Ther (1944) 82:377-390.

(56) References Cited

OTHER PUBLICATIONS

Drews-Bankiewicz M, et al. "Contrast Sensitivity in Patients with Nuclear Cataracts". Arch. Ophthalmol 1992; 110: 953-959.
Drugbank Online "Phentolamine", DrugBank Accession No. DB0692, 9 pages. Retrieved online: https://go.drugbank.com/drugs/DB00692. Accessed Aug. 25, 2022.
Drum B, Cologero D, Rorer E. "Assessment of visual performance in the evaluation of new medical products", Drug Discoveries Today: Technologies. Lam K, Timmerman H, eds. Elsevier. 2007; 4(2) 55-61.
Drummond, P. D. "The Effect of Light Intensity and Dose of Dilute Pilocarpine Eyedrops on Pupillary Constriction in Healthy Subjects," Am. J. Ophthalmol., vol. 112, No. 2, p. 195-199, (1991).
Du H, Ren J, Wang S, He L. "Cell membrane chromatography competitive binding analysis for characterization of α1A adrenoreceptor binding interactions", Anal Bioanal Chem. 2011;400(10):3625-3633.
Dungan, K.W., et al., "Amidephrine-I: Pharmacologic Characterization of a Sympathomimetic Alkylsulfonamidophenethanolamine," Int. J. Neuropharmacol., vol. 4, p. 219-234 (1965).
Durand-Cavagna G, Hubert MF, Gerin G, Molon-Noblot S. "Spontaneous pre-Descemet's membrane corneal opacities in rabbits",Lab Anim Sci 1998;48(3):310-3.
Edgar, D. F. et al., "Effects of dipivefrin and pilocarpine on pupil diameter, automated perimetry and Log MAR acuity," Graefe's Arch. Clin. Exp. Ophthalmol., vol. 237, p. 117-124 (1999).
Elliott DB, Patla A, Bullimore MA. "Improvements in clinical and functional vision and perceived visual disability after first and second eye cataract surgery", Brit J Ophthalmol. 1997; 81:889-895.
Elliott DB, Sanderson K, Conkey A. "The reliability of the Pelli-Robson chart", Ophthalmology and Physiological Optics. 1990; 10:21-24.
Enroth-Cugell, C Robson JG. "The contrast sensitivity of retinal ganglion cells of the cat", J Physiol. 1966; 187: 517-552.
European Glaucoma Society Terminology and Guidelines for Glaucoma, 4th Edition—Chapters: Treatment principles and options. Br J Ophthalmol 2017;101(6):130-95.
European Search Report dated Jun. 21, 2016 from European Patent Application 14746208.9 (6 pages). European Search Report for Patent No. 147462089.
Eydelman M, Hilmantel G, Tarver ME, Hofmeister EM, May J, Hammel K, et al. "Symptoms and Satisfaction of Patients in the Patient-Reported Outcomes With Laser In Situ Keratomileusis (PROWL) Studies", JAMA Ophthalmol. 2017;135(1):13-22.
Fan TY, Wall GM, Sternitzke K, Bass L, Morton AB, Muegge E. "Improved high-performance liquid chromatographic determination of pilocarpine and its degradation products in ophthalmic solutions importance of octadecylsilane col. choice", Journal of Chromatography A. 1996;740(2):289-295.
Fan-Paul, N. I., Li, J., Miller, J. S., & Florakis, G. J. (2002). "Night vision disturbances after corneal refractive surgery", Surv Ophthalmol, 47(6), 533-546.
Fejer, T. P., & Girgis, R. (1992). "Night myopia: implications for the young driver", Clinical J Ophthalmol, 27(4), 172-176. Retrieved from https://www.ncbi.nlm.nih.gov/pubmed/1633588.
Foster, S., Patel, R., Khatri, A., et al. (2022). "MIRA-4, Clinical Trial Evaluating the Safety and Efficacy of Phentolamine Ophthalmic Solution for Reversal of Pharmacologically Induced Mydriasis in Pediatric Subjects Aged 3-11 Years", AAOpt Annual Meeting, Abstract ID 10569, 1 page.
Fricke, T. R., Tahhan, N., Resnikoff, S., Papas, E., Burnett, A., Ho, S. M., Naidoo, K. S. (2018). "Global Prevalence of Presbyopia and Vision Impairment from Uncorrected Presbyopia: Systematic Review, Meta-analysis, and Modelling", Ophthalmology, 125(10), 1492-1499.
Gambill, H. D et al., "Mydriatic Effect of Four Drugs Determined With Pupillograph," Arch. Ophthal., vol. 77, p. 740-746 (1967).
Geyer, 0. et al., "The additive miotic effects of dapiprazole and pilocarpine," Graefe's Arch. Clin. Exp. Ophthalmol., vol. 233, p. 448-451 (1995).

Gilmartin, B. et al., "Reversal of tropicamide mydriasis with single instillations of pilocarpine can induce substantial pseudo-myopia in young adults," Ophthal. Physiol. Opt., vol. 15, No. 5, pp. 475-479 (1995).
Ginsburg AP. Contrast sensitivity and functional vision in Functional Vision. In Packer, M, editor. Functional Vision. Philadelphia (PA) Lippincott Williams & Wilkins; 2003; p. 5-15. (Int. Ophthalmol Clin, vol. 43).
Ginsburg AP, "Contrast sensitivity: determining the visual quality and function of cataract, intraocular lenses and refractive surgery", CurrOpin Ophthalmol. 2006; 17:19-26.
Ginsburg AP. Vision Channels, Contrast Sensitivity and Functional Vision in Human Vision and Electronic Imaging IX. Rogowitz, BE, ed. SPIE-IS&T. 2004; 529:215-25.
Giovannitti, J. A., Jr., Thoms, S. M., & Crawford, J. J. (2015). "Alpha-2 adrenergic receptor agonists: a review of current clinical applications", Anesth Prog, 62(1), 31-39.
Glycerol (Glycerin, Anhydrous, ACS) Safety Data Sheet by CCI (year 2012), Generic Names: 1,2,3-Propanetriol; Glycerol; Manufacturer: Columbus Chemical Industries, Inc., 6 pages.
Godbillon J. "Determination of the major metabolite of phentolamine in human plasma and urine by high performance liquid chromatography", J Chromatography. 1981; 222:461-466.
Goel, M., Picciani, R. G., Lee, R. K., & Bhattacharya, S. K. (2010). "Aqueous humor dynamics: a review", Open Ophthalmol J, 4, 52-59.
Goertz AD, Stewart WC, Burns WR, Stewart JA, Nelson LA. "Review of the impact of presbyopia on quality of life in the developing and developed world", Acta Ophthalmol. 2014;92(6):497-500.
Goldstein I. "Oral phentolamine: an alpha-1, alpha-2 adrenergic antagonist for the treatment of erectile dysfunction", Int J Impot Res. 2000;12(S1):S75-S80.
Gomez-Gomar A, Gonzalez-Aubert M, Costa-Segarra J. "HPLC method for the simultaneous determination of pilocarpine, isopilocarpine, pilocarpic acid and isopilocarpic acid", Journal of Pharmaceutical and Biomedical Analysis. 1989;7(12):1729-1734.
Hadzija et al., "Physicochemical Stability of Papaverine Hydrochloride-Phentolamine Mesylate Mixtures Used for Intracavernous Injection: A Preliminary Evaluation," The Journal of Urology, (1988), vol. 140, p. 64-65.
Hara, H. et al., "Bunazosin, a Selective α1-Adrenoceptor Antagonist, as an Antiglaucoma Drug: Effects on Ocular Circulation and Retinal Neuronal Damage," Cardiovascular Drug Reviews, (2005), vol. 23, No. 1, p. 43-56.
Hays RD, Tarver ME, Spritzer KL, Reise S, Hilmantel G, Hofmeister EM, et al. "Assessment of the Psychometric Properties of a Questionnaire Assessing Patient-Reported Outcomes With Laser In Situ Keratomileusis (PROWL)", JAMA Ophthalmol. 2017;135(1):3-12.
Hersh, E. V., Lindemeyer, R., Berg, J. H., Casamassimo, P. S., Chin, J., Marberger, A., Group, P. S. (2017). "Phase Four, Randomized, Double-Blinded, Controlled Trial of Phentolamine Mesylate in Two- to Five-year-old Dental Patients", Pediatr Dent, 39(1), 39-45.
Hersh EV, LindemeyerRG. "Phentolamine mesylate for accelerating recovery from lip and tongue anesthesia", Dent Clin North Am (2010) 54:631-642.
Hill, C. E., Purves, R. D., Watanabe, H., & Burnstock, G. (1976). "Specificity of innervation of iris musculature by sympathetic nerve fibres in tissue culture", Pflugers Arch, 361(2), 127-134.
Hogan, T. S., McDaniel, D. D., Bartlett, J. D., Hart, K. K., & Paggiarino, D. A. (1997). "Dose response study of dapiprazole HCI in the reversal of mydriasis induced by 2.5% phenylephrine", J Ocul Pharmacol Ther, 13(4), 297-302.
Holladay, J. T., Meyer, A., & Pitlick, B. (2018). Phentolamine Mesylate Ophthalmic Solution Once Daily Reduces Pupil Diameter and Improves Night Vision Disturbances. AAO Annual Meeting, PA025, 14 pages.
Holladay JT et al. "Functional vision and corneal changes after laser in situ keratomileusis determined by contrast sensitivity, glare testing and corneal topography", J Cataract Refract Surg. 1999; 25:664-669.

(56) References Cited

OTHER PUBLICATIONS

Holve D, Mundwiler K, Schuh J, Pritt S. "Optical Coherence Tomography and Slit Lamp Imaging of Corneal Dystrophy in the Dutch Belted Rabbit", vol. 8, p. 9, Unpublished data.

Hong, D., & Tripathy, K. (2020) "Tropicamide" [Updated Jul. 4, 2020], In: StatPearls [Internet], Treasure Island (FL): StatPearls Publishing, 2020, 4 pages.

Howe JW, Mitchell KW. "The objective assessment of contrast sensitivity function by electrophysiological means", Brit J Ophthalmology. 1984; 68:626-638.

International Search Report and Written Opinion of the International Searching Authority, the U.S. Patent & Trademark Office, for International Application No. PCT/US2014/014067, dated May 21, 2014, 8 pages.

International Search Report and Written Opinion of the International Searching Authority, the U.S. Patent & Trademark Office, for International Application No. PCT/US2014/014070, dated Apr. 15, 2014, 10 pages.

Ishikawa, H., Miller, D. D., & Patil, P. N. (1996). "Comparison of post-junctional alphaadrenoceptors in iris dilator muscle of humans, and albino and pigmented rabbits", Naunyn Schmiedebergs Arch Pharmacol, 354(6), 765-772.

ISOPTO (2010). Isopto® Carpine (Pilocarpine Hydrochloride Ophthalmic Solution) FDA Documents 1%, 2% and 4%. Highlights of Prescribing Information/ / Package Insert / Label, 2009, Revised Jun. 2010, Alcon Laboratories, Inc. Fort Worth, TX, USA, 5 pages.

Israilov S et al. "Intracavernous injections for erectile dysfunction in patients with cardiovascular diseases and failure or contraindications for sildenafil citrate", Intl J Impot Res. 2002; 14:38-43.

Jackson, M. et al. (2022). "A Combination of Phentolamine Eye Drops and Low Dose Pilocarpine Improves Near Vision in VEGA-1 Phase 2 Presbyopia Trial", AAO Annual Meeting, Abstract ID 30070768, 8 pages.

Jacobson, D. M. and Olson, K. A. "Influence of Pupil Size, Anisocoria, and Ambient Light on Pilocarpine Miosis: Implications for Supersensitivity Testing," Ophthalmology, vol. 100, No. 2, pp. 275-280 (1992).

Johnston, C. "Relief for Patients Troubled by Night-Vision Complaints: Presented at AAO", PeerVoice Publication, dated Oct. 21, 2010, 1 page.

Kan X, Zheng S I., Zhou C y. UPLC-MS/MS Determination of Phentolamine in Human Plasma and its Application to a Pharmacokinetic Study. Drug Res (Stuttg). 2014;64(11):607-612.

Kannarr, S., Brigell, M., Patel, R., et al. (2022). LYNX-1: A Pivotal Phase 3 Randomized Placebo-Controlled Trial of Phentolamine Ophthalmic Solution in Subjects with Dim Light Vision Disturbance. AAOpt Annual Meeting, Abstract ID 10526, 1 page.

Karpecki P.M., Foster S.A., Montaquila S.M., et al. "Phentolamine eye drops reverse pharmacologically induced mydriasis in a randomized phase 2b trial", Optom Vis Sci. 2021,98(3):234-242.

Kass, M. A., Heuer, D. K., Higginbotham, E. J., Johnson, C. A., Keltner, J. L., Miller, J. P., Gordon, M. O. (2002). "The Ocular Hypertension Treatment Study: a randomized trial determines that topical ocular hypotensive medication delays or prevents the onset of primary open-angle glaucoma", Arch Ophthalmol, 120(6), 701-713; discussion 829-730.

Kato COS, Shimizu K, Kamiya K, Ishikawa H, Igarashi A. Effects of brimonidine tartrate 0.1% ophthalmic solution on the pupil, refraction, and light reflex. Sci Rep. 2018;8(1):9003. doi:10.1038/s41598-018-27436-8.

Katz, J., Lazar, E., Kolli, A., et al. (2022). "VEGA-1: Phentolamine Ophthalmic Solution as a Single Agent Improves Distance-Corrected Near Visual Acuity in Patients with Presbyopia", ARVO Annual Meeting, Abstract ID 3712883, 1 page.

Kennedy et al. "High-performance liquid chromatographic analysis of pilocarpine hydrochloride, isopilocarpine, pilocarpic acid and isopilocarpic acid in eye-drop preparations", Journal of Chromatography A, vol. 212, Issue 3, 1981, pp. 331-338.

Kerger, B.D., James, R.C., & Robberts, S.M. (1988) "An assay for phentolamine using high performance liquid chromotography with electrochemical detection", Analyt Biochem, 170:145-151.

Kesler A, Shemesh G, Rothkoff L, Lazar M. "Effect of brimonidine tartrate 0.2% ophthalmic solution on pupil size", Journal of Cataract and Refractive Surgery. 2004;30(8):1707-1710.

Kiel, J. W., & Reitsamer, H. A. (2007). "Paradoxical effect of phentolamine on aqueous flow in the rabbit", J Ocul Pharmacol Ther, 23(1), 21-26.

Kimlin, J. A., Black, A. A., & Wood, J. M. (2017). "Nighttime Driving in Older Adults: Effects of Glare and Association With Mesopic Visual Function", Invest Ophthalmol Vis Sci, 58(5), 2796-2803.

Kinney M, Johnson AD, Reddix M, McCann MB. "Temporal Effects of 2% Pilocarpine Ophthalmic Solution on Human Pupil Size and Accommodation" Military Medicine. 2020;185(Supplement 1):435-442.

Kirsten R, Nelson K, Kirsten D, Heintz B. Clinical pharmacokinetics of vasodilators. Part II. Clin Pharmacokinet (1998) 35(1):9-36.

Klein, B. E., Klein, R., Sponsel, W. E., Franke, T., Cantor, L. B., Martone, J., & Menage, M. J. (1992). "Prevalence of glaucoma. The Beaver Dam Eye Study", Ophthalmology, 99(10), 1499-1504.

Kobayashi, H., Kobayashi, K., & Okinami, S. (2004). Efficacy of bunazosin hydrochloride 0.01% as adjunctive therapy of latanoprost or timolol. J Glaucoma, 13(1), 73-80.

Konno F, Takayanagi I. "Characterization of postsynaptic alpha-1 adrenoceptors in the rabbit iris dilator smooth muscle", Naunyn Schmiedebergs Arch Pharmacol (1986) 333:271-276.

Koss, M. C., & Gherezghiher, T. (1988). "Pharmacological characterization of alphaadrenoceptors involved in nictitating membrane and pupillary responses to sympathetic nerve stimulation in cats", Naunyn Schmiedebergs Arch Pharmacol, 337(1), 18-23.

Krupin, T., Feitl, M., & Becker, B. (1980). "Effect of prazosin on aqueous humor dynamics in rabbits", Arch Ophthalmol, 98(9), 1639-1642.

Kupersmith MJ et al. "Contrast sensitivity loss in multiple sclerosis", Invest Ophthalmol Vis Sci. 1984;25:632-639.

Kwon, Y. H., Fingert, J. H., Kuehn, M. H., & Alward, W. L. (2009). "Primary open-angle glaucoma", N Engl J Med, 360(11), 1113-1124.

Langevin, N.E., Schafer, K.A., Turner, O.C., McPherson, B.J., Rose, R.E. (2018) "Historical Data: Histopathology Lesions Observed in the Eyes of Control Rabbits in Topical Ocular Administration and Contact Lens Studies", Toxicologic Pathology 46(7): 799-820.

Leavitt, J. A. et al., "Pupillary Response to Four Concentrations of Pilocarpine in Normal Subjects: Application to Testing for Adie Tonic Pupil," American Journal of Ophthalmology, vol. 133, pp. 333-336 (2002).

Lee JH, You YS, Choe CM, Lee ES. "Efficacy of brimonidine tartrate 0.2% ophthalmic solution in reducing halos after laser in situ keratomileusis", Journal of Cataract and Refractive Surgery. 2008;34(6):963-967.

Lewis, R. A. et al."Fixed-dose combination of AR-13324 and latanoprost: A doublemasked, 28-day, randomised, controlled study in patients with open-angle glaucoma or ocular hypertension". Br. J. Ophthalmol. 100, 339-344 (2016).

Lin, Shi-Bei-Lei; Hu, Chao; Qin, Yong-Ping; Miao, Jia; Feng, Shi-Yin; Shu, Shi-Qing et al. (2018) "Pharmacokinetics Study of Phentolamine Mesylate Injection in Healthy Volunteers",Journal of Sichuan University, Medical Science edition 49 (6), pp. 929-933. (Abstract Attached).

Liu, J. C., Green, W., Van Stavern, G. P., & Culican, S. M. (2017). "Assessing the utility of 2.5% phenylephrine for diagnostic pupillary dilation", Can J Ophthalmol, 52(4), 349-354.

Lograno, M. D., & Reibaldi, A. (1986). "Receptor-responses in fresh human ciliary muscle". Br J Pharmacol, 87(2), 379-385.

Marshall, L. L., Hayslett, R. L., & Stevens, G. A. (2018). "Therapy for Open-Angle Glaucoma", Consult Pharm, 33(8), 432-445.

Martell, A.E. "Chelates of Ascorbic Acid Formation and Catalytic Properties," Advances in Chemistry, vol. 200, pp. 153-187 (1982).

Martinez, C. E., Applegate, R. A., Klyce, S. D., McDonald, M. B., Medina, J. P., & Howland, H. C. (1998). "Effect of pupillary dilation

(56) References Cited

OTHER PUBLICATIONS on corneal optical aberrations after photo refractive keratectomy", Arch Ophthalmol, 116(8), 1053-1062.

Marx-Gross S, Krummenauer F, Dick BH, Pfeiffer N. "Brimonidine versus dapiprazole: Influence on pupil size at various illumination levels", Journal of Cataract and Refractive Surgery. 2005;31(7):1372-1376.

Matsuura K, Kuwano M, Takashina H. "Determination of pilocarpine in aqueous humour by liquid chromatography—atmospheric pressure chemical ionization mass spectrometry", Journal of Chromatography B: Biomedical Sciences and Applications. 1993;621(2):173-180.

McAuliffe-Curtin D, Buckley C. "Review of alpha adrenoceptor function in the eye", Eye (1989) 3:472-476.

McDonald, M. B., Pitlick, W., D.R., V., Meyer, A. R., & E.D., D. (Oct. 18, 2010). "Phentolamine Mesylate Treatment of Severe Night Vision Complaints", AAO Abstracts, PO433, 3 pages.

McDonald, M., Kolli A., Patel, R., el al. (2022). "MIRA-3: A 2nd Phase 3 Randomized Placebo-Controlled Trial of Phentolamine Ophthalmic Solution to Reverse Pharmacologically Induced Mydriasis", ASCRS Annual Meeting, Paper ID 81993, 12 pages.

McDonald MB, Pitlick WH, VanDevanter DR, et al. "Phentolamine mesylate treatment of severe night-vision complaints", Presented at: Annual Meeting of the American Society of Cataract and Refractive Surgery; Mar. 25-29, 2011; San Diego, CA, 17 pages.

McDonnell, P. J., Lee, P., Spritzer, K., Lindblad, A. S., & Hays, R. D. (2003). "Associations of presbyopia with vision-targeted health-related quality of life", Arch Ophthalmol, 121(11), 1577-1581.

McMahon CG A pilot study of the role of intracavernous injection of vasoactive intestinal peptide (VIP) and phentolamine mesylate in the treatment of erectile dysfunction. Int J Impot Res. 1996; 4:233-6.

Mittag, T. W., Tormay, A., Severin, C., & Podos, S. M. (1985). "Alpha-adrenergic antagonists: correlation of the effect on intraocular pressure and on alpha 2-adrenergic receptor binding specificity in the rabbit eye", Exp Eye Res, 40(4), 591-599.

Mohammadpour M, Heidari Z, Hashemi H. "Updates on Managements for Keratoconus", J Curr Ophthalmol 2018;30(2): 110-124.

Molinari, J. F., Johnson, M. E., & Carter, J. (1994). "Dapiprazole clinical efficiency for counteracting tropicamide 1%", Optometry and Vision Science, 71(5), 319-322.

Monestam, E., & Lundqvist, B. (2006). "Long-time results and associations between subjective visual difficulties with car driving and objective visual function 5 years after cataract surgery", J Cataract Refract Surg, 32(1), 50-55.

Montes-Mico R, Espana E, Bueno I, et al. "Visual performance with multifocal intraocular lenses: Mesopic contrast sensitivity under distance and near conditions", Ophthalmology 2004;111:85-96.

Montes-Mico R et al. "Choice of spatial frequency for contrast sensitivity evaluation after corneal refractive surgery", J. Refract. Surg. 2001; 17:646-651.

Moore CP, Dubietzig R, Glaza SM. "Anterior Corneal Dystrophy of American Dutch Belted Rabbits: Biomicroscopic and Histopathologic Findings",Vet. Pathol. 1987; 24:28-33.

Moore, P. A.; Hersh, E. V.; Papas, A. S.; Goodson, J. M.; Yagiela, J. A.; Rutherford, B. et al. (2008): "Pharmacokinetics of lidocaine with epinephrine following local anesthesia reversal with phentolamine mesylate", Anesth.Prog. 55 (2), pp. 40-48.

Motolko MA, Phelps CD. "Contrast sensitivity in asymmetric glaucoma", Int Ophthalmol. 1984; 7(1):45-59.

MUCOMYST® (acetylcysteine solution), Prescribing Information/Package Insert/Label, 2001, Revised Oct. 2006, Bristol-Myers Squibb Company, 18 pages.

Muftuoglu, 0. et al., "Drug-induced intraocular lens movement and near visual acuity after AcrySof intraocular lens implantation," J. Cataract. Refract. Surg., vol. 31, pp. 1298-1305 (2005).

Murphy et al., "How red is white eye? Clinical grading of normal conjunctival hyperemia", May 2007, Eve, vol. 21, No. 4, p. 633-638.

Nagasubramanian S. "A Comparison of the Ocular Hypotensive Efficacy, Safety and Acceptability of Brimonidine 0.2% Twice Daily Versus Pilocarpine 2.0% Thrice Daily as Adjunct Therapy with Beta-Blockers", Glaucoma Update VI. Springer Berlin Heidelberg; 2000:203-208.

Nakamura S, Taniguchi T, Suzuki F, Akagi Y, Muramatsu 1."Evaluation of alpha-1 adrenoceptors in the rabbit iris: pharmacological characterization and expression of mRNA", Br J Ophthalmol (1999) 127:1367-1374.

National Institutes of Health "NIH urges dilated eye exams to detect glaucoma", Accessed Apr. 24, 2020, 3 pages. Retrieved online: https://www.nih.gov/news-events/news-releases/nih-urges-dilated-eye-exams-detect-glaucoma.

National Institutes of Health, "Visual acuity test", Feb. 23, 2015, online://medlineplus.qov/ency/article/003396.htm, 3 pages.

Neonatal Intensive Care Unit, "Edrophonium",Children's Hospital London Health Science Centre, Manual, May 26, 2011, 4 pages.

Nielsen, C. B., & Nielsen, P. J. (1985). "Effect of alpha- and beta-receptor active drugs on corneal thickness", Acta Ophthalmol (Copenh), 63(3), 351-354.

Noordam A, Maat L, Beyerman HC. "Quantitative Determination of Pilocarpine, Isopilocarpine, Pilocarpic Acid, and Isopilocarpic Acid in Clinical Ophthalmic Pilocarpine Formulations by Reversed-Phase Liquid Chromatography", Journal of Pharmaceutical Sciences. 1981;70(1):96-97.

Notice of Intention to Grant a Patent dated Apr. 10, 2019 from European Patent Application 14746208.9 (162 pages). European Search Report for Patent No. 147462089 Ocularis 2018.

Nyman, Neal Optometrist*; Keates, Edwin U. "Effects of Dapiprazole on the Reversal of Pharmacologically Induced Mydriasis",Optometry and Vision Science: Sep. 1990, vol. 67, Issue 9, p. 705-709.

Ogura T, Katayama E, Mitsui T, et al. "Properties of [3H]bunazosin binding in rat kidney", Clin Ther. 1988;10(5):559-567.

OraVerse® (2016a). OraVerse (phentolamine mesylate) FDA Documents injection, Highlights of Prescribing Informationpackage Insert / Label, Initial US approval 1952, Revised Mar. 2016, Septodont, Inc., 4 pages.

OraVerse® (2016b). OraVerse FDA Documents. FDA approves OraVerse for pediatric dental patients 3 years and older, May 2016, 3 pages.

OraVerse® (phentolamine mesylate) injection; Prescribing Information/ Package Insert/Label, Initial US Approval: 1952; Novalar2008, 2 pages.

OraVerse Summary Basis of Approval (SBA). Clinical pharmacology and biopharmaceutics review. Application No. 22-159; 2007, 73 pages. https://www.accessdata.fda.gov/drugsatfda docs/nda/2008/022159s000_ClinPharmR. Pdf.

Oshika, T., Araie, M., Sugiyama, T., Nakajima, M., & Azuma, I. (1991)."Effect of bunazosin hydrochloride on intraocular pressure and aqueous humor dynamics in normotensive human eyes", Arch Ophthalmol, 109(11), 1569-1574.

Oshika, T. et al. "Incidence of intraoperative floppy iris syndrome in patients on either systemic or topical alpha(1)-adrenoceptor antagonist", Am. J. Ophthalmol. 143, 150-151 (2007).

Owsley C. "Contrast Sensitivity", Ophthalmol Clin N Am. 2003; 16:171-177.

Owsley C, Sloane, ME. "Contrast sensitivity, acuity, and the perception of real-world' targets", Brit J Ophthalmology. 1987; 71:791-796.

Ozulken, K. et al., "Effect of topical pilocarpine on refractive surgery outcomes," Int. Ophthalmol., vol. 40, pp. 733-740 (2020).

Padma-Nathan, H., Goldstein, I., Klimberg, I., Coogan, C., Auerbach, S., Lammers, P., & Vasomax Study, G. (2002). Long-term safety and efficacy of oral phentolamine mesylate (Vasomax) in men with mild to moderate erectile dysfunction, Int J Impot Res, 14(4), 266-270.

Park, S. Y., Choi, Y. J., Jung, J. W., Choi, M., Kim, E. K., Seo, K. Y., & Kim, T. I. (2019). "Clinical Efficacy of Pinhole Soft Contact Lenses for the Correction of Presbyopia", Semin Ophthalmol, 34(2), 106-114.

Pepose, J. (2021c). "Phase 2 Clinical Trial To Evaluate The Efficacy Of Phentolamine Ophthalmic Solution And Low-Dose Pilocarpine For The Treatment Of Presbyopia" AAO Annual Meeting. Abstract ID 30068457, 10 pages.

(56) References Cited

OTHER PUBLICATIONS

Pepose J, Brigell M, Lazar E, Heisei C, Yousif J, Rahmani K, Kolli A, Hwang M, Mitrano C, Lazar A, Charizanis K, Sooch M, McDonald M. "A randomized phase 2 clinical trial of phentolamine mesylate eye drops in patients with severe night vision disturbances", BMC Ophthalmology Oct. 8, 2022;22(1):402, 11 pages.
Pepose, J., Kolli, A., Patel, R., et al. (2022a). "Phentolamine Ophthalmic Solution as a Single Agent Improves Distance-Corrected Near Visual Acuity in Patients with Presbyopia", ASCRS Annual Meeting, Paper ID 80665, 11 pages.
Pepose, J., Kolli, A., Patel, R., et al. (2022b). VEGA-1: Phentolamine Ophthalmic Solution in combination with Low Dose Pilocarpine Improves Distance-Corrected Intermediate Visual Acuity in Patients with Presbyopia. ARVO Annual Meeting, Abstract ID 3707817.
Pepose J, P. B., Meyer A, Jaber R, Charizanis K, Lazar E, Sooch M, Slonim C. (2020). "Phentolamine mesylate ophthalmic solution provides long lasting pupil modulation and improves visual acuity", The Association for Research in Vision and Ophthalmology Meeting.
Pepose J.S., Charizanis K., Sooch M.P., et al. (2021a). "Phase 3 clinical trial to evaluate the efficacy of phentolamine ophthalmic solution on the reversal of pharmacologically induced mydriasis Paper #76599", The American Society of Cataract and Refractive Surgery Meeting, 15 pages.
Pepose J.S., Charizanis K., Sooch M.P., et al. (2021b) "Phase 2 Clinical Trial to Evaluate the Efficacy of Phentolamine Ophthalmic Solution and Low-Dose Pilocarpine for the Treatment of Presbyopia", Paper #76645. The American Society of Cataract and Refractive Surgery Meeting, 13 pages.
Pepose JS, Hartman PJ, DuBiner HB, et al. "Phentolamine mesylate ophthalmic solution provides lasting pupil modulation and improves near visual acuity in presbyopic glaucoma patients in a randomized phase 2b clinical trial" Clin Ophthalmol. 2021;15:79-91.
Peter JVS, Lambrecht LJ, Gunderson BW, Andersen SA, Gallagher SC, Swan SK. "Pharmacokinetics of Pilocarpine in Subjects with Varying Degrees of Renal Function", Journal of Clinical Pharmacology. 2000;40(12 Pt 2):1470-1475.
Pop, M., & Payette, Y. (2004). "Risk factors for night vision complaints after LASIK for myopia", Ophthalmology, 111(1), 3-10.
Poulet, F. M., Berardi, M. R., Halliwell, W., Hartman, B., Auletta, C., & Bolte, H. (2004). "Development of hibernomas in rats dosed with phentolamine mesylate during the 24-month carcinogenicity study", Toxicol Pathol, 32(5), 558-566.
Prata TS, Palmiero PM, Angelilli A, et al. "Iris morphologic changes related to alpha (1) adrenergic receptor antagonists: implications for intraoperative floppy iris syndrome", Ophthalmology 2009;116:877-81.
Puell, M. C., Palomo, C., Sanchez-Ramos, C., & Villena, C. (2004). "Mesopic contrast sensitivity in the presence or absence of glare in a large driver population", Graefes Arch Clin Exp Ophthalmol, 242(8), 755-761.
Radi, Z., Bartholomew, P., Elwell, M., & Vogel, W. M. (2013). "Comparative pathophysiology, toxicology, and human cancer risk assessment of pharmaceutical-induced hibernoma", Toxicol Appl Pharmacol, 273(3), 456-463.
Rahman MQ, Ramaesh K, Montgomery DM. "Brimonidine for glaucoma", Expert Opinion on Drug Safety. 2010;9(3):483-491.
Ramsay, D. A. "Dilute Solutions of Phenylephrine and Pilocarpine in the Diagnosis of Disordered Autonomic Innervation of the Iris: Observations in Normal Subjects, and in the Syndromes of Horner and Holmes-Adie," Journal of the Neurological Sciences, vol. 73, pp. 125-134 (1986).
Regan D et al. "Visual acuity and contrast sensitivity in multiple sclerosis—hidden visual loss: an auxiliary diagnostic test" Brain. 1977; 100(3):563-79.
Regitine. (1998). Regitine FDA Documents. Highlights of Prescribing Information, 38 pages.
Regitine—phentolamine mesylate injection, powder, lyophilized, for suspension; label/prescribing information; Novartis Pharmaceuticals Corporation (1998), 5 pages.
Rengstorff, R. H., & Doughty, C. B. (1982). "Mydriatic and cycloplegic drugs: a review of ocular and systemic complications", Am J Optom Physiol Opt, 59(2), 162-177. Retrieved from https://www.ncbi.nlm.nih.gov/pubmed/7039329.
Rev-Eyes. (2013). Federal Register; 78(92):27971 "Determination that Rev-Eyes (dapiprazole hydrochloride ophthalmic solution), 0.5%, was not withdrawn from sale for reasons of safety or effectiveness", 1 page.
Rev-Eyes® dapiprazole hydrochloride ophthalmic solution 0.5%. NDA 019849. Dec. 31, 1990, 1 page.
Rev-Eyes® (dapiprazole hydrochloride ophthalmic solution) Ophthalmic Eyedrops 0.5% (Bausch & Lomb), Drug Reference Encyclopedia, 1998, 4 pages, U.S. Pat. No. 4,252,721, Manufactured by Abbott Laboratories, North Chicago, IL. Retrieved online: https://theodora.com/drugs/rev_eyes_ophthalmic_eyedrops_05_bausch_lomb.html.
Rev-Eyes™, in Physicians' Desk Reference for Ophthalmic Medicines (2003) Thomson PDR, p. 258.
Rhopressa (2017). "Rhopressa pharmacology/toxicology NDA review and evaluation", United States Food and Drug Administration; Non-Clinical Review(s), Application No. 2082540rig1s000, 95 pages.
Richards, D.A., Woodings, E.P., Prichard, B.N. "Circulatory and alpha-adrenoceptor blocking effects of phentolamine", Br J Clin Pharmacol (1978) 5(6):507-513.
Ridder WH et al. "Contrast Sensitivity and Tear Layer Aberrometry in Dry Eye Patients", Optometry and Vision Sciences 2009; 86:E1059-1068.
Robin, A. L., Novack, G. D., Covert, D. W., Crockett, R. S., & Marcic, T. S. (2007). "Adherence in glaucoma: objective measurements of once-daily and adjunctive medication use", Am J Ophthalmol, 144(4), 533-540.
Romero-Jimenez, M., Santodomingo-Rubido, J., & Wolffsohn, J. S. (2010). "Keratoconus: A Review", Contact & Lens Anterior Eye, 33(4), 157-166.
Rosen, Emanuel S. "Night vision disturbance",, Journal of Cataract & Refractive Surgery. 2005;31(2):247-9.
Rutherford, B., Zeller, J. R., & Thake, D. (2009) "Local and systemic toxicity of intraoral submucosal injections of phentolamine mesylate (OraVerse)", Anesth Prog, 56(4), 123-127.
Rutkowski et al., "Mydriasis and Increased Intraocular Pressure", Arch Ophthalmol. 1972;87(1):21-24.
Safety and Efficacy of Ophthalmic Phentolamine Mesylate in Glaucoma, a clinical study description, NCT03960866, available from clinicaltrials.gov on line on May 23, 2019, 5 pages.
Safety and Efficacy of Ophthalmic Phentolamine Mesylate in Glaucoma, a clinical study description, NCT03960866, available from clinicaltrials.gov online on Oct. 14, 2019, 5 pages.
Safety and Efficacy of Ophthalmic Phentolamine Mesylate to Reverse Pharmacologically Induced Mydriasis, a clinical study description, available from clinicaltrials.gov online on Oct. 14, 2019; NCT04024891, 7 pages.
Sandoval HP et al. "Comparison of visual outcomes, photopic contrast sensitivity, wavefront analysis,and patient satisfaction following cataract extraction and IOL implantation: aspheric vs spherical acrylic lenses", Eye 2008; 22:1469-1475.
Schallhorn, S. C., Tanzer, D. J., Kaupp, S. E., Brown, M., & Malady, S. E. (2009). "Comparison of night driving performance after wavefront-guided and conventional LASIK for moderate myopia" Ophthalmology, 116(4), 702-709.
Serie JB, Katz LJ, McLaurin E, Heah T, Ramirez-Davis N, Usner DW, et al. "Two Phase 3 Clinical Trials Comparing the Safety and Efficacy of Netarsudil to Timolol in Patients With Elevated Intraocular Pressure: Rho Kinase Elevated IOP Treatment Trial 1 and 2 (ROCKET-1 and ROCKET-2)", Am J Ophthalmol. 2017;186:116-27.
Shah, B., Hubbard, B., Stewart-Jones, J. H., Edgar, D. F., & Turner, P. (1989). "Influence of thymoxamine eye-drops on the mydriatic effect of tropicamide and phenylephrine alone and in combination", Ophthalmic Physiol Opt, 9(2), 153-155.
Shemesh G, Moisseiev E, Lazar M, Kesler A. "Effect of brimonidine tartrate 0.10% ophthalmic solution on pupil diameter", Journal of Cataract and Refractive Surgery. 2011;37(3):486-489.
Sherwood, M. B. et al. "Twice-Daily 0.2% Brimonidine-0.5% Timolol Fixed-Combination Therapy vs Monotherapy With Timolol

(56) References Cited

OTHER PUBLICATIONS or Brimonidine in Patients With Glaucoma or Ocular Hypertension", Arch. Ophthalmol. 124, 1230 (2006).
Shiau, T., Armogan, N., Yan, D. B., Thomson, H. G., & Levin, A. V. (2012). "The role of episcleral venous pressure in glaucoma associated with Sturge-Weber syndrome", J AAPOS, 16(1), 61-64.
Shiose, Y., Kitazawa, Y., Tsukahara, S., Akamatsu, T., Mizokami, K., Futa, R., Kosaki, H. (1991). "Epidemiology of glaucoma in Japan—a nationwide glaucoma survey", Jpn J Ophthalmol, 35(2), 133-155. Retrieved from https://www.ncbi.nlm.nih.gov/pubmed/1779484.
Silva, L. F. G.; Moraes, M. O.; Santana, G. S. M.; Frota Bezerra, F. A.; Nucci, G. de; Moraes, M. E. A. (2004) "Phentolamine bioequivalence study", In Int. J Clin. Pharmacol. Ther 42 (1), pp. 43-49.
Single Dose Study of Phentolamine Mesylate Eye Drops in Patients With Severe Night Vision Disturbances, Study NCT 04004507, Aug. 1, 2019, Ocuphire Pharma, Inc., 5 pages.
Sioufi A, Pommier F, Mangoni P. Gauron, S, & Metayer, J-P. (1981) "Gas chromatographic determination of phentolamine (Regitine®) in Human Plasma", J Chromat. 222429-435.
Smith, S. A. et al., "An increased effect of pilocarpine on the pupil by application of the drug in oil," British Journal of Ophthalmology, vol. 62, pp. 314-317 (1978).
Soli et al., "Vasoactive Cocktails for Erectile Dysfunction: Chemical Stability of PGE1, Papaverine and Phentolamine," The Journal of Urology, (1998), vol. 160, pp. 551-555.
Sommer, A., Tielsch, J. M., Katz, J., Quigley, H. A., Gottsch, J. D., Javitt, J., & Singh, K. (1991). "Relationship between intraocular pressure and primary open angle glaucoma among white and black Americans" The Baltimore Eye Survey. Arch Ophthalmol, 109(8), 1090-1095.
Steiner, T. F. (2013). "State of independent optometry: optometry dominates primary eyecare", Review of Optometric Business, 2 pages.
Steinhauer, S. R., Siegle, G. J., Condray, R., & Pless, M. (2004). "Sympathetic and parasympathetic innervation of pupillary dilation during sustained processing", Int J Psychophysiol, 52(1), 77-86.
Sternitzke KD, Fan TY, Dunn L. "High-performance liquid chromatographic determination of pilocarpitie hydrochloride and its degradation products using a /I-cyclodextrin column", Journal of Chromatography, 1992;10(589):159-164.
Suzuki F, Taniguchi T, Nakamura S, et al. "Distribution of alpha-1 adrenoceptor subtypes in RNA and protein in rabbit eyes", Br J Ophthalmol (2002) 135:600-608.
Takayanagi, I., Shiraishi, K., & Kokubu, N. (1992). "Alpha 1B-adrenoceptor mechanisms in rabbit iris dilator", Jpn J Pharmacol, 59(3), 301-305.
Tang W et al. "Visual performance of lasik patients", Ann Acad Med Singapore 2006; 35:541-546.
Tanzer JM, Kramer PA, Schulman P, Willard AK. A Pharmacokinetic and Pharmacodynamic Study of Intravenous Pilocarpine in Humans. J Dent Res. 1995;74(12):1845-1849.
Taylor SH, Sutherland GR, MacKenzie GJ, Staunton HP, and Donald KW. The circulatory effects of phentolamine in man. Circulation (1965) 31:741-754. doi: 10.1161/01.cir.31.5.741.
Tecnis Multifocal Intraocular Lens, Models ZM900 and ZMAOO, Premarket Approval Application No. P080010; CDRH/FDA, Summary of Safety and Effectiveness (SSED), 2009, 38 pages. Retrieved online: https://www.accessdata.fda.gov/cdrh_docs/pdf8/P080010B.pdf.
Tham, Y. C., Li, X., Wong, T. Y., Quigley, H. A., Aung, T., & Cheng, C. Y. (2014). Global prevalence of glauco ma and projections of glaucoma burden through 2040: a systematic review and meta-analysis. Ophthalmology, 121(11), 2081-2090. doi:10.1016/j.ophtha.2014.05.013.
Thomas J. "Normal and amblyopic contrast sensitivity functions in central and peripheral retinas", Invest. Ophthalmol Visual Sci. 1978; 17:746-753.
Thompson, H. S. "Adie's Syndrome: Some New Observations," Tr. Am. Ophth. Soc., vol. 75, pp. 587-626 (1977).
Thordsen JE, Bower KS, Warren BB, Stutzman R. "Miotic effect of brimonidine tartrate 0.15% ophthalmic solution in normal eyes", Journal of Cataract and Refractive Surgery. 2004;30(8):1702-1706.
Torre et al., "Impaired Cerebromicrovascular Perfusion Summary of Evidence in Support of Its Causality in Alzheimer's Disease", Annals of the New York Academy of Sciences, Jan. 25, 2006, p. 136-152.
Trew, D. R., Wright, L. A., & Smith, S. E. (1991). "Ocular responses in healthy subjects to topical bunazosin 0.3%—an alpha 1-adrenoceptor antagonist", Br J Ophthalmol, 75(7), 411-413.
Troy et al., "Remington: The Science and Practice of Pharmacy", 21st ed., University of the Sciences, Philadelphia, Pennsylvania, 2006, p. 1032.
Tu et al., "Stability of papaverine hydrochloride and phentolamine mesylate in injectable mixtures," American Journal of Hospital Pharmacy, (1987), vol. 44, pp. 2524-2527.
Tuan, KA and Liang, J. "Improved contrast Sensitivity and visual acuity after wavefrontguided laser in situ Keratomileusis: In-depth statistical analysis", J. Cataract Refract. Surg. 2006; 32:215-230.
Tucker, J., & Charman, W. N. (1975). "The depth-of-focus of the human eye for Snellen letters", Am J Optom Physiol Opt, 52(1), 3-21.
Uusitalo, H. "The effect of autonomic receptor blockers on the ocular response to topical chemical irritation", Acta Physiol Scand. 1984; 121:1-8.
Van Alphen, G. W. (1976). "The adrenergic receptors of the intraocular muscles of the human eye", Invest Ophthalmol, 15(6), 502-505. Retrieved online: https://www.ncbi.nlm.nih.gov/pubmed/6403.
Van Demark RE, Hewitt C, Smith VJ. "Phentolamine rescue for digital ischemia following lidocaine with epinephrine local anesthesia: Case presentation, review of the literature and treatment options", S D Med (2021) 74:532-536.
Van Gaalen KW, Jansonius NM, Koopmans SA, et al. "Relationship between contrast sensitivity and spherical aberration: comparison of 7 contrast sensitivity tests with natural and artificial pupils in healthy eyes", J Cataract Refract Surg. 2009; 35:47-56.
Vivacy, "Stylage", retrieved from http://www.stylage.eu/technology.html on May 27, 2016, 4 pages.
Volkers, ACW et al. "Spatial contrast sensitivity and the diagnosis of amblyopia", Brit J Ophthalmology. 1987; 71:58-65.
Wachler, BS et al. "Comparison of Contrast Sensitivity in Different Soft Contact Lenses and Spectacles", CLAO Journal. 1999; 25;48-50.
Wachler, BS, et al. "Role of Clearance and treatment zones in refractive surgery", J. Cataract Refract. Surg. 1999; 25:16-23.
Wallace Dinsmore W, Wyllie MG. "Vasoactive intestinal polypeptide/phentolamine for intracavernosal injection in erectile dysfunction", BJU Int (2008) 102:933-937.
Wang et al., "Degradation Kinetics of Phentolamine Hydrochloride in Solution," Journal of Pharmaceutical Sciences, (1988), vo. 77, No. 11, pp. 972-976.
Wang, J., Song, Y., Ren, B., Sun, N., Yu, Y., & Hu, H. (2003). "Different effects of topical prazosin and pilocarpine on uveoscleral outflow in rabbit eyes", China Academic Journal Electronic Publishing House, 19(3), 191-194.
Wang YH, Huang LC, Tsai SHL, Chen YJ, Wu CL, Kang YN. "Risk of intraoperative floppy iris syndrome among selective alpha-1 blockers-A consistency model of 6,488 cases" Frontiers in Medicine Aug. 30, 2022;9:941130, 12 pages.
Waring GO, Price FW, Wirta D, et al. "Safety and Efficacy of AGN-190584 in Individuals With Presbyopia: The Gemini 1 Phase 3 Randomized Clinical Trial", JAMA Ophthalmol. 2022;140(4):363-371.
West SK, Rubin GS, Broman AT, Munoz B, Bandeen-Roche K, Turano K. "How does visual impairment affect performance on tasks of everyday life?" The SEE Project. Salisbury Eye Evaluation. Arch Ophthalmol. 2002;120(6):774-80.
Wiederholt, M., Thieme, H. & Stumpff, F. "The regulation of trabecular meshwork and ciliary muscle contractility", Prog. Retin. Eye Res. 19, 271-95 (2000).
Wilson D.T., Hardisty, J.F., Hayes, J.R. and Wilson, N.H. (2014) "Short-term, subchronic and chronic toxicology studies", Hayes'

(56) References Cited

OTHER PUBLICATIONS

Principles and Methods of Toxicology. Hayes, A.W. and Kruger, C.L. (Eds). Chap. 24, CRC Press, N.Y., pp. 1205-1249.
Wood, J. M., Garth, D., Grounds, G., McKay, P., & Mulvahil, A. (2003). "Pupil dilatation does affect some aspects of daytime driving performance", Br J Ophthalmol, 87(11), 1387-1390.
Wright MM, Skuta GL, Drake MV, Chang LF, Rabbani R, Musch DC, et al. "Time course of thymoxamine reversal of phenylephrine-induced mydriasis", Arch Ophthalmol. 1990;108(12):1729-32.
Xu R., Pepose, J. (2022). What is Optimal Pupil Size? Cataract & Refractive Surgery Today. 10 pages. Retrieved online: https://crstoday.com/articles/jan-2022/what-is-the-optimal-pupil-size/.
Xu R., Thibos L., Bradley A., "Effect of Target Luminance on Optimum Pupil Diameter for Presbyopic Eyes", Optometry and Vision Science. 2016;91(11):1409-19.
Yoshitomi, T., Ito, Y., & Inomata, H. (1985). "Adrenergic excitatory and cholinergic inhibitory innervations in the human iris dilator", Exp Eye Res, 40(3), 453-459.
Yu, Y., & Koss, M. C. (2002) "alpha(1A)-adrenoceptors mediate sympathetically evoked pupillary dilation in rats", J Pharmacol Exp Ther, 300(2), 521-525.
Zetterstrom, C., & Hahnenberger, R. (1988). "Pharmacological characterization of human ciliary muscle adrenoceptors in vitro", Exp Eye Res, 46(3), 421-430.
Zimmerman, T. J. "Pilocarpine," Ophthalmology, vol. 88, No. 1, p. 85-88 (1981).

\* cited by examiner

HIGHLY PURE PHENTOLAMINE MESYLATE AND METHODS FOR MAKING SAME

CROSS-REFERENCE TO RELATED APPLICATIONS

This application claims the benefit of U.S. Provisional Application No. 63/189,839, filed May 18, 2021, and of Chinese Application No. 202110679032.9, filed Jun. 18, 2021, the disclosure of each of which is incorporated by reference herein in its entirety.

FIELD OF THE INVENTION

This invention provides methods for synthesizing phentolamine mesylate from phentolamine and methanesulfonic acid in the presence of acetone and water. The methods of the present invention provide highly pure phentolamine mesylate. The invention also provides highly pure phentolamine mesylate.

BACKGROUND OF THE INVENTION

Phentolamine mesylate is a nonselective alpha adrenergic receptor antagonist approved for use by the Food and Drug Administration (FDA) for reversing soft-tissue anesthesia. Phentolamine mesylate was also approved by the FDA for use in preventing or controlling hypertensive episodes in patients with pheochromocytoma and for treatment of dermal necrosis following intravenous administration or extravasation of norepinephrine.

Phentolamine mesylate continues to be studied for new indications. Thus, an improved synthesis of phentolamine to produce highly pure product is desired.

SUMMARY OF THE INVENTION

The present invention provides methods for making phentolamine mesylate, comprising:
(a) allowing Compound 1

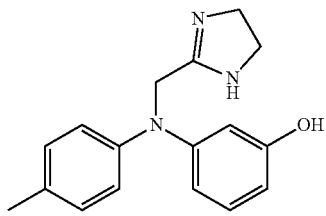

to react with methanesulfonic acid in the presence of acetone and water under conditions effective to make a first mixture comprising phentolamine mesylate;
(b) admixing to the first mixture and methyl t-butyl ether to make a second mixture; and
(c) allowing the phentolamine mesylate to precipitate from the second mixture (each method being a "synthesis method of the invention").

The present invention further provides phentolamine mesylate that is made by a synthesis method of the invention, has a purity obtainable by a synthesis method of the invention or exhibits an X-ray powder diffraction (XRPD) pattern obtainable by a synthesis method of the invention (the phentolamine mesylate being a "compound of the invention").

The present invention further provides phentolamine mesylate that exhibits an XRPD pattern comprising a peak at about 6.87±0.2 degrees 2-theta, a peak at about 20.32±0.2 degrees 2-theta, and a peak at about 21.36±0.2 degrees 2-theta.

The present invention further provides compositions comprising an effective amount of a compound of the invention (each composition being a "composition of the invention").

The present invention further provides methods for inhibiting contraction of smooth muscle of the iris, comprising administering to a subject in need thereof an effective amount of a compound of the invention.

The present invention further provides methods for reducing pupil diameter, comprising administering to a subject in need thereof an effective amount of a compound of the invention.

The present invention further provides methods for improving visual contrast sensitivity or visual acuity, comprising administering to a subject in need thereof an effective amount of a compound of the invention.

The present invention further provides methods for treating a dim or night vision disturbance, comprising administering to a subject in need thereof an effective amount of a compound of the invention.

The present invention further provides methods for treating or reversing pharmacologically induced mydriasis, comprising administering to a subject in need thereof an effective amount of a compound of the invention.

The present invention further provides methods for treating presbyopia, comprising administering to a subject in need thereof an effective amount of a compound of the invention.

Each of the methods for inhibiting contraction of smooth muscle of the iris, reducing pupil diameter, improving visual contrast sensitivity or visual acuity, treating a dim or night vision disturbance, treating or reversing pharmacologically induced mydriasis or treating presbyopia is a "therapeutic method of the invention".

DETAILED DESCRIPTION OF THE INVENTION

Definitions

Figure 1:
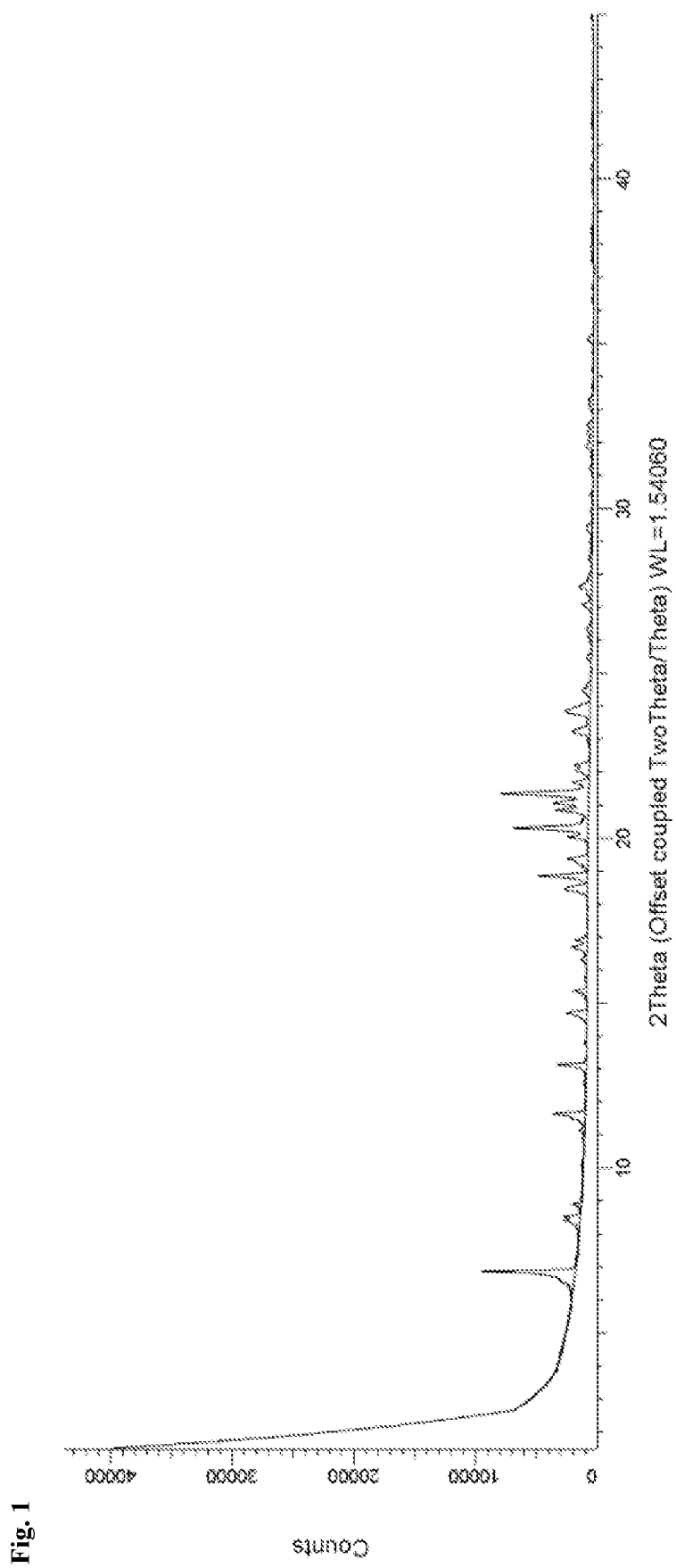
FIG. 1 shows an XRPD pattern of a phentolamine mesylate obtained as described in Example 2.

The term "about" when immediately preceding a numerical value means±up to 20% of the numerical value. For example, "about" a numerical value means±up to 20% of the numerical value, in some embodiments, ±up to 19%, ±up to 18%, ±up to 17%, ±up to 16%, ±up to 15%, ±up to 14%, ±up to 13%, ±up to 12%, ±up to 11%, ±up to 10%, ±up to 9%, ±up to 8%, ±up to 7%, ±up to 6%, ±up to 5%, ±up to 4%, ±up to 3%, ±up to 2%, ±up to 1%, ±up to less than 1%, or any other value or range of values therein.

Throughout the present specification, numerical ranges are provided for certain quantities. These ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "pharmaceutically acceptable salt" includes both an acid and a base addition salt. Pharmaceutically acceptable salts can be obtained by reacting a compound of the invention functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Pharmaceutically acceptable salts can also be obtained by reacting a compound of the invention functioning as an acid, with an inorganic or organic base to form a salt, for example, salts of sodium, potassium, lithium, ammonium, calcium, magnesium, iron, zinc, copper, manganese, aluminum, ammonia, isopropylamine, trimethylamine, etc. In some embodiments, the pharmaceutically acceptable salt is a zinc salt. Those skilled in the art will further recognize that pharmaceutically acceptable salts can be prepared by reaction of the compounds of the invention with an appropriate inorganic or organic acid or base via any of a number of known methods.

The term "solvate" refers to a solvation complex. Solvates can be formed by solvation (the combination of solvent molecules with molecules or ions of the compounds of the invention), or a solvate can be an aggregate that comprises a solute ion or molecule or a solvent molecule. The solvent can be water, in which case the solvate is a hydrate. Examples of hydrates include, but are not limited to, a hemihydrate, monohydrate, dihydrate, trihydrate, hexahydrate, etc. The solvate can be formed via hydration, including via absorption of moisture. A pharmaceutically acceptable salt can also be a solvate. Where a solvate is obtained via crystallization from a solvent, the solvent can be an alcohol, such as methanol or ethanol; an aldehyde; a ketone, such as acetone; or an ester, such as ethyl acetate.

The term "effective amount" refers to an amount of a compound of the invention that is effective to inhibit contraction of smooth muscle of the iris, reduce pupil diameter, improve visual contrast sensitivity or visual acuity, treat a dim or night vision disturbance or treat or reverse pharmacologically induced mydriasis in a subject in need thereof.

All weight percentages (i.e., "% by weight" and "wt. %" and w/w) referenced herein, unless otherwise indicated, are relative to the total weight of the mixture or composition, as the case may be.

As used herein, an "impurity" is a compound or substance other than phentolamine mesylate.

As used herein, "isolated" means isolated from a chemical synthesis reaction mixture. In some embodiments, isolated phentolamine mesylate is at least 95% pure and comprises no more than 5% of one or more impurities. By "is at least x % pure" means that a compound of the invention includes no more than (100−x) % of one or more impurities. In some embodiments, isolated phentolamine mesylate is at least 96%, at least 97%, at least 98%, or at least 99% pure, and comprises no more than 4%, no more than 3%, no more than 2%, or no more than 1% of an impurity, respectively. In some embodiments, the one or more impurities, if any, are present in the phentolamine mesylate as a percent by weight. In some embodiments, the one or more impurities, if any, are present in the phentolamine mesylate as a percent by mole. In some embodiments, the one or more impurities, if any, are present in the phentolamine mesylate as a percent by volume.

As used herein, "substantially the same as" when used in connection with an XRPD pattern means that that each peak of the XRPD pattern differs from a respective peak of a stated reference compound by no more than ±0.2 degrees 2-theta, in some embodiments, no more than ±0.1 degree 2-theta.

As used herein, "substantially the same as" when used in connection with a DSC thermogram means that that each peak of the DSC thermogram differs from a respective peak of a stated reference compound by no more than ±3° C., in some embodiments, no more than ±2° C.

As used herein, "substantially the same as" when used in connection with a TG thermogram means that that each peak of the TG thermogram differs from a respective peak of a stated reference compound by no more than ±3° C., in some embodiments, no more than ±2° C.

Synthesis Methods of the Invention

The present invention provides methods for making phentolamine mesylate, comprising:
(a) allowing Compound 1

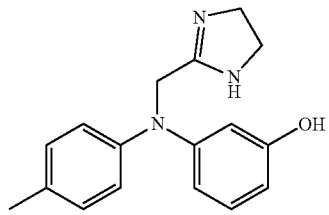

1 to react with methanesulfonic acid in the presence of acetone and water under conditions effective to make a first mixture comprising phentolamine mesylate;
(b) admixing the first mixture and methyl t-butyl ether to make a second mixture; and
(c) allowing the phentolamine mesylate to precipitate from the second mixture.

In some embodiments of the synthesis methods of the invention, the methods further comprise the step of: (d) isolating the phentolamine mesylate from the second mixture, wherein the isolating provides isolated phentolamine mesylate. In some embodiments, the isolating is filtering, and the isolated phentolamine mesylate is filtered phentolamine mesylate. In some embodiments, the filtered phentolamine mesylate is washed with methyl t-butyl ether.

In some embodiments of the synthesis methods of the invention, the methods further comprise the step of: (e) drying the isolated phentolamine mesylate to provide dried phentolamine mesylate. In some embodiments, the isolated phentolamine or filtered phentolamine is dried using a rotary evaporator. In some embodiments, the isolated phentolamine or filtered phentolamine is dried using a rotary evaporator and at a temperature of about 30° C. to about 50°

C. In some embodiments, the isolated phentolamine or filtered phentolamine is dried using a rotary evaporator and at a temperature of about 30° C. to about 40° C. In some embodiments, the drying comprises lyophilizing. In some embodiments, the drying comprises drying using a rotary evaporator and subsequently lyophilizing. In some embodiments, the drying is continued until a weight loss on drying is not more than 0.5% of the weight of the isolated phentolamine mesylate subjected to drying.

In some embodiments, the drying is performed at a pressure ranging from about 0.001 mbar to about 1000 mbar. In some embodiments, the drying is performed at a pressure ranging from about 1 mbar to about 1000 mbar. In some embodiments, the drying is performed at a pressure ranging from about 1 mbar to about 500 mbar. In some embodiments, the drying is performed at a pressure ranging from about 1 mbar to about 200 mbar. In some embodiments, the drying is performed at a pressure ranging from about 1 mbar to about 100 mbar. In some embodiments, the drying is performed at a pressure ranging from about 1 mbar to about 50 mbar. In some embodiments, the drying is performed at a pressure ranging from about 0.001 mbar to about 1 mbar. In some embodiments, the drying is performed at a pressure ranging from about 0.001 mbar to about 0.75 mbar. In some embodiments, the drying is performed at a pressure ranging from about 0.001 mbar to about 0.5 mbar. In some embodiments, the drying is performed at a pressure ranging from about 0.005 mbar to about 0.75 mbar. In some embodiments, the drying is performed at a pressure ranging from about 0.01 mbar to about 0.75 mbar. In some embodiments, the drying is performed at a pressure ranging from about 0.05 mbar to about 0.75 mbar. In some embodiments, the drying is performed at a pressure ranging from about 0.05 mbar to about 0.5 mbar. In some embodiments, the drying is performed at a pressure of about 40 mbar.

In some embodiments, the lyophilizing is performed at a temperature of about −78° C. to about 0° C. In some embodiments, the lyophilizing performed at a temperature of about −50° C. to about 0° C. In some embodiments, the lyophilizing performed at a temperature of about −50° C. to about −10° C. In some embodiments, the lyophilizing performed at a temperature of about 0° C., about −5° C., about −10° C., about −15° C., about −20° C., about −25° C., about −30° C., about −35° C., about −40° C., about −45° C., about −50° C., about −55° C., about −60° C., about −65° C., about −70° C., about −75° C., or about −78° C. In some embodiments, the temperature is the temperature inside a vessel that contains the phentolamine mesylate. In some embodiments, the temperature is the temperature outside of a vessel that contains the phentolamine mesylate. In some embodiments, the temperature is that of a cooling bath or an interior of a cooling jacket or refrigeration device.

In some embodiments, the lyophilizing is performed at a pressure ranging from about 0.001 mbar to about 1000 mbar. In some embodiments, the lyophilizing is performed at a pressure ranging from about 1 mbar to about 1000 mbar. In some embodiments, the lyophilizing is performed at a pressure ranging from about 1 mbar to about 500 mbar. In some embodiments, the lyophilizing is performed at a pressure ranging from about 1 mbar to about 200 mbar. In some embodiments, the lyophilizing is performed at a pressure ranging from about 1 mbar to about 100 mbar. In some embodiments, the lyophilizing is performed at a pressure ranging from about 1 mbar to about 50 mbar. In some embodiments, the lyophilizing is performed at a pressure ranging from about 0.001 mbar to about 1 mbar. In some embodiments, the lyophilizing is performed at a pressure ranging from about 0.001 mbar to about 0.75 mbar. In some embodiments, the lyophilizing is performed at a pressure ranging from about 0.001 mbar to about 0.5 mbar. In some embodiments, the lyophilizing is performed at a pressure ranging from about 0.005 mbar to about 0.75 mbar. In some embodiments, the lyophilizing is performed at a pressure ranging from about 0.01 mbar to about 0.75 mbar. In some embodiments, the lyophilizing is performed at a pressure ranging from about 0.05 mbar to about 0.75 mbar. In some embodiments, the lyophilizing is performed at a pressure ranging from about 0.05 mbar to about 0.5 mbar. In some embodiments, the lyophilizing is performed at a pressure of about 40 mbar.

In some embodiments, the lyophilizing is performed at a pressure ranging from about 50 mTorr to about 400 mTorr. In some embodiments, the lyophilizing is performed at a pressure ranging from about 100 mTorr to about 350 mTorr. In some embodiments, the lyophilizing is performed at a pressure ranging from about 100 mTorr to about 300 mTorr. In some embodiments, the lyophilizing is performed at a pressure ranging from about 100 mTorr to about 200 mTorr. In some embodiments, the lyophilizing is performed at a pressure of about 50 mTorr, about 75 mTorr, about 100 mTorr, about 125 mTorr, about 150 mTorr, about 175 mTorr, about 200 mTorr, about 225 mTorr, about 250 mTorr, about 275 mTorr, about 300 mTorr, about 325 mTorr, about 350 mTorr, about 375 mTorr, or about 400 mTorr.

In some embodiments, the lyophilizing is performed for about 30 minutes to about 7 days. In some embodiments, the lyophilizing is performed for about 30 minutes to about 5 days. In some embodiments, the lyophilizing is performed for about 30 minutes to about 3 days. In some embodiments, the lyophilizing is performed for about 30 minutes to about 24 hours. In some embodiments, the lyophilizing is performed for about 30 minutes to about 12 hours. In some embodiments, the lyophilizing is performed for about 30 minutes to about 6 hours. In some embodiments, the lyophilizing is performed for about 30 minutes to about 3 hours. In some embodiments, the lyophilizing is performed for about 30 minutes, about 45 minutes, about 60 minutes, about 75 minutes, about 90 minutes, about 105 minutes, about 120 minutes, about 135 minutes, about 150 minutes, about 165 minutes, or about 180 minutes. In some embodiments, the lyophilizing is performed for about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 26 hours, about 28 hours, about 30 hours, about 32 hours, about 34 hours, about 36 hours, about 38 hours, about 40 hours, about 42 hours, about 44 hours, about 46 hours, about 48 hours, about 50 hours, about 52 hours, about 54 hours, about 56 hours, about 58 hours, about 60 hours, about 62 hours, about 64 hours, about 66 hours, about 68 hours, about 70 hours, or about 72 hours. In some embodiments, the time described herein for the lyophilization is the time for one or more lyophilization cycles. In one embodiment, the lyophilizing is performed using 1, 2, 3, 4, 5, 6, 7, 8, 9, or 10 lyophilization cycles. In one embodiment, the lyophilizing comprises an annealing step.

In some embodiments, the lyophilizing is performed with stirring. In some embodiments, the lyophilizing is performed without stirring.

In some embodiments of the synthesis methods of the invention, the ratio of acetone to water is about 5:1 acetone:

water by volume to about 15:1 acetone:water by volume. In some embodiments, the ratio of acetone to water is about 10:1 acetone:water by volume to about 12:1 acetone:water by volume. In some embodiments, the ratio of acetone to water is about 11:1 acetone:water by volume. In some embodiments, the ratio of acetone to water is about 5:1, about 6:1, about 7:1, about 8:1, about 9:1, about 10:1, about 11:1, about 12:1, about 13:1, about 14:1, or about 15:1 acetone:water by volume.

In some embodiments of the synthesis methods of the invention, the concentration of Compound 1 is about 0.2 moles/liter of the acetone and water to about 0.4 moles/liter of the acetone and water. In some embodiments, the concentration of Compound 1 is about 0.3 moles/liter of the acetone and water. In some embodiments, the concentration of Compound 1 is about 0.2 moles/liter, about 0.25 moles/liter, about 0.3 moles/liter, about 0.35 moles/liter, or about 0.4 moles/liter of the acetone and water.

In some embodiments of the synthesis methods of the invention, the acetone and water does not comprise a detectable amount of an alcohol solvent. In some embodiments of the synthesis methods of the invention, the acetone and water comprise less than about 1%, less than about 0.5%, less than about 0.1%, or less than about 0.01% of an alcohol solvent by weight of the acetone and water. In some embodiments of the synthesis methods of the invention, the first mixture does not comprise a detectable amount of an alcohol solvent. In some embodiments of the synthesis methods of the invention, the first mixture comprises less than about 1%, less than about 0.5%, less than about 0.1%, or less than about 0.01% of an alcohol solvent by weight of the first mixture. In some embodiments of the synthesis methods of the invention, the second mixture does not comprise a detectable amount of an alcohol solvent. In some embodiments of the synthesis methods of the invention, the second mixture comprises less than about 1%, less than about 0.5%, less than about 0.1%, or less than about 0.01% of an alcohol solvent by weight of the second mixture. In some embodiments of the synthesis methods of the invention, the acetone and water, the first mixture and the second mixture do not comprise a detectable amount of an alcohol solvent. In some embodiments, the synthesis methods of the invention are performed in the absence of a detectable amount of an alcohol solvent. In some embodiments of the synthesis methods of the invention, the acetone and water, the first mixture and the second mixture comprise less than about 1%, less than about 0.5%, less than about 0.1%, or less than about 0.01% of an alcohol solvent by weight of the acetone and water, the first mixture, or the second mixture. In some embodiments, the synthesis methods of the invention are performed in the absence of a detectable amount of an alcohol solvent. In some embodiments, the alcohol solvent is isopropanol, n-propanol, ethanol, or methanol.

In some embodiments of the synthesis methods of the invention, the acetone and water does not comprise toluene. In some embodiments of the synthesis methods of the invention, the first mixture does not comprise toluene. In some embodiments of the synthesis methods of the invention, the second mixture does not comprise toluene. In some embodiments of the synthesis methods of the invention, the acetone and water, the first mixture and the second mixture do not comprise toluene. In some embodiments, the synthesis methods of the invention are performed in the absence of a detectable amount of toluene. In some embodiments, the synthesis methods of the invention are performed in the absence of a detectable amount of an alcohol solvent and toluene.

In some embodiments of the synthesis methods of the invention, the acetone and water is at or is adjusted to a temperature of about 15° C. to about 25° C. In some embodiments, the acetone and water is at or is adjusted to a temperature of about 15° C. to about 25° C. immediately before allowing Compound 1 to react with methanesulfonic acid.

In some embodiments of the synthesis methods of the invention, Compound 1 and the acetone and water form a solution, and the methanesulfonic acid is added to the solution. In some embodiments, Compound 1 and the acetone and water form a solution, and the methanesulfonic acid is added dropwise to the solution. In some embodiments, Compound 1 and the acetone and water form a solution, the methanesulfonic acid is added to the solution and the addition of methanesulfonic acid causes the temperature of the solution to rise to about 40° C. to about 50° C. In some embodiments, Compound 1 and the acetone and water form a solution, the methanesulfonic acid is added to the solution and after the complete addition of methanesulfonic acid, the first mixture is allowed to stir for about 30 minutes. In some embodiments, Compound 1 and the acetone and water form a solution, the methanesulfonic acid is added to the solution and after the complete addition of methanesulfonic acid, the first mixture is allowed to stir for at least about 30 minutes.

In some embodiments of the synthesis methods of the invention, Compound 1 and the acetone and water form a solution, and the solution is added to the methanesulfonic acid. In some embodiments, Compound 1 and the acetone and water form a solution, and the solution is added dropwise to the methanesulfonic acid. In some embodiments, Compound 1 and the acetone and water form a solution, the solution is added to the methanesulfonic acid and the addition of the solution causes the temperature of the solution to rise to about 40° C. to about 50° C. In some embodiments, Compound 1 and the acetone and water form a solution, the solution is added to the methanesulfonic acid and after the complete addition of solution, the first mixture is allowed to stir for about 30 minutes. In some embodiments, Compound 1 and the acetone and water form a solution, the solution is added to the methanesulfonic acid and after the complete addition of solution, the first mixture is allowed to stir for at least about 30 minutes.

In some embodiments of the synthesis methods of the invention, Compound 1 and the acetone and water form a suspension, and the methanesulfonic acid is added to the suspension. In some embodiments, Compound 1 and the acetone and water form a suspension, and the methanesulfonic acid is added dropwise to the suspension. In some embodiments, Compound 1 and the acetone and water form a suspension, the methanesulfonic acid is added to the suspension and the addition of methanesulfonic acid causes the temperature of the suspension to rise to about 40° C. to about 50° C. In some embodiments, Compound 1 and the acetone and water form a suspension, the methanesulfonic acid is added to the suspension and after the complete addition of methanesulfonic acid, the first mixture is allowed to stir for about 30 minutes. In some embodiments, Compound 1 and the acetone and water form a suspension, the methanesulfonic acid is added to the suspension and after the complete addition of methanesulfonic acid, the first mixture is allowed to stir for at least about 30 minutes.

In some embodiments of the synthesis methods of the invention, Compound 1 and the acetone and water form a suspension, and the suspension is added to the methanesulfonic acid. In some embodiments, Compound 1 and the acetone and water form a suspension, and the suspension is added dropwise to the methanesulfonic acid. In some embodiments, Compound 1 and the acetone and water form a suspension, the suspension is added to the methanesulfonic acid and the addition of the suspension causes the temperature of the suspension to rise to about 40° C. to about 50° C. In some embodiments, Compound 1 and the acetone and water form a suspension, the suspension is added to the methanesulfonic acid and after the complete addition of suspension, the first mixture is allowed to stir for about 30 minutes. In some embodiments, Compound 1 and the acetone and water form a suspension, the suspension is added to the methanesulfonic acid and after the complete addition of suspension, the first mixture is allowed to stir for at least about 30 minutes.

In some embodiments of the synthesis methods of the invention, the first mixture is clear. In this context, "clear" means that all visible solids are dissolved completely or are no longer visible. In some embodiments, the first mixture is heated at about 45° C. and allowed to stir until the first mixture becomes clear. In some embodiments, the first mixture is heated at about 45° C. and allowed to stir at about 45° C. until the first mixture becomes clear.

In some embodiments of the synthesis methods of the invention, the methods comprise allowing 1 molar equivalent of Compound 1 to react with about 0.9 molar equivalent to about 1.5 molar equivalent of methanesulfonic acid. In some embodiments, the synthesis methods comprise allowing 1 molar equivalent of Compound 1 to react with about 1.1 molar equivalent of methanesulfonic acid. In some embodiments, the synthesis methods comprise allowing 1 molar equivalent of Compound 1 to react with about 0.9 molar equivalent, about 1.0 molar equivalent, about 1.1 molar equivalent, about 1.2 molar equivalent, about 1.3 molar equivalent, about 1.4 molar equivalent, or about 1.5 molar equivalent of methanesulfonic acid.

In some embodiments, the admixing comprises adding the methyl t-butyl ether to the first mixture. In some embodiments, the admixing comprises adding the first mixture to the methyl t-butyl ether.

In some embodiments of the synthesis methods of the invention, the first mixture is at or is adjusted to a temperature of about 15° C. to about 25° C. immediately before admixing the first mixture and methyl t-butyl ether.

In some embodiments of the synthesis methods of the invention, allowing phentolamine mesylate to precipitate from the second mixture comprises cooling the second mixture to a temperature of about 15° C. to about –25° C. In some embodiments, allowing phentolamine mesylate to precipitate from the second mixture comprises cooling the second mixture to a temperature of about 15° C. to about –15° C. In some embodiments, allowing phentolamine mesylate to precipitate from the second mixture comprises cooling the second mixture to a temperature of about 5° C. to about –25° C. In some embodiments, allowing phentolamine mesylate to precipitate from the second mixture comprises cooling the second mixture to a temperature of about 5° C. to about –15° C. In some embodiments, allowing phentolamine mesylate to precipitate from the second mixture comprises cooling the second mixture to a temperature of about 15° C. to about 8° C. In some embodiments, allowing phentolamine mesylate to precipitate from the second mixture comprises cooling the second mixture to a temperature of about 14° C. to about 5° C. In some embodiments, allowing phentolamine mesylate to precipitate from the second mixture comprises cooling the second mixture to a temperature of about 0° C. to about –15° C. In some embodiments, allowing phentolamine mesylate to precipitate from the second mixture comprises cooling the second mixture to a temperature of about 3° C. to about –3° C. In some embodiments, allowing phentolamine mesylate to precipitate from the second mixture comprises cooling the second mixture to a temperature of about 0° C. In some embodiments, allowing phentolamine mesylate to precipitate from the second mixture comprises cooling the methyl t-butyl ether-diluted mixture to a temperature of about –20° C.

In some embodiments of the synthesis methods of the invention, allowing phentolamine mesylate to precipitate comprises cooling the second mixture to a first temperature of about 15° C. to about –15° C., allowing the second mixture to stir at the first temperature for about 1 hour, and then further cooling the second mixture to a second temperature of about –20° C. In some embodiments, the first temperature is about 15° C. to about –5° C. In some embodiments, the first temperature is about 15° C. to about 0° C. In some embodiments, the first temperature is about 14° C. to about 8° C. In some embodiments, the first temperature is about 3° C. to about –3° C.

In some embodiments, the second mixture is cooled to the first temperature at an average rate of about 0.5° C./min to about 2° C./min. In some embodiments, the second mixture is cooled to the first temperature at an average rate of about 1° C./min to about 1.5° C./min. In some embodiments, the second mixture is cooled to the first temperature at an average rate of about 1.33° C./min. In some embodiments, cooling the second mixture to the first temperature takes about 5 minutes to about 60 minutes. In some embodiments, cooling the second mixture to the first temperature takes about 10 minutes to about 45 minutes. In some embodiments, cooling the second mixture to the first temperature takes about 10 minutes to about 30 minutes. In some embodiments, cooling the second mixture to the first temperature takes about 15 minutes.

In some embodiments, the second mixture is cooled from the first temperature to the second temperature at an average rate of about 0.5° C./min to about 2° C./min. In some embodiments, the second mixture is cooled from the first temperature to the second temperature at an average rate of about 0.75° C./min to about 1.5° C./min. In some embodiments, the second mixture is cooled to the second temperature from the first temperature at an average rate of about 1° C./min. In some embodiments, cooling the second mixture to the second temperature from the first temperature takes about 5 minutes to about 60 minutes. In some embodiments, cooling the second mixture to the second temperature from the first temperature takes about 10 minutes to about 45 minutes. In some embodiments, cooling the second mixture to the second temperature from the first temperature takes about 10 minutes to about 30 minutes. In some embodiments, cooling the second mixture to the second temperature from the first temperature takes about 20 minutes.

In some embodiments of the synthesis methods of the invention, the methods are performed in the absence of a detectable amount of an alkyl methanesulfonate. In some embodiments, the methods do not make an alkyl methanesulfonate, e.g., as a by-product or degradation product. In some embodiments, a compound of the invention does not comprise an alkyl methanesulfonate.

In some embodiments, the purity of the methanesulfonic acid is at least about 95% (weight %) and the methanesulfonic acid comprises no more than about 5% of an impurity (weight %) of the methanesulfonic acid. In some embodiments, the purity of the methanesulfonic acid is at least about 97% (weight %) and the methanesulfonic acid comprises no more than about 3% of an impurity (weight %) of the methanesulfonic acid. In some embodiments, the purity of the methanesulfonic acid is at least about 98% (weight %) and the methanesulfonic acid comprises no more than about 2% of an impurity (weight %) of the methanesulfonic acid. In some embodiments, the purity of the methanesulfonic acid is at least about 99% (weight %) and the methanesulfonic acid comprises no more than about 1% of an impurity (weight %). In some embodiments, the methanesulfonic acid does not comprise a detectable amount of an alkyl methanesulfonate. In some embodiments, the impurity is determined by high-performance liquid chromatography (HPLC). In some embodiments, the impurity is determined by gas chromatography (GC).

In some embodiments, the purity of the acetone is at least about 95% (weight %) and acetone comprises no more than about 5% of an impurity (weight %) of the acetone. In some embodiments, the purity of the acetone is at least about 97% (weight %) and acetone comprises no more than about 3% of an impurity (weight %) of the acetone. In some embodiments, the purity of the acetone is at least about 98% (weight %) and acetone comprises no more than about 2% of an impurity (weight %) of the acetone. In some embodiments, the purity of the acetone is at least about 99% (weight %) and acetone comprises no more than about 1% of an impurity (weight %) of the acetone. In some embodiments, the acetone does not comprise a detectable amount of an alkyl methanesulfonate. In some embodiments, the impurity is determined by high-performance liquid chromatography (HPLC). In some embodiments, the impurity is determined by gas chromatography (GC).

In some embodiments, the purity of the water is at least about 95% (weight %) and water comprises no more than about 5% of an impurity (weight %) of the water. In some embodiments, the purity of the water is at least about 97% (weight %) and water comprises no more than about 3% of an impurity (weight %) of the water. In some embodiments, the purity of the water is at least about 98% (weight %) and water comprises no more than about 2% of an impurity (weight %) of the water. In some embodiments, the purity of the water is at least about 99% (weight %) and water comprises no more than about 1% of an impurity (weight %) of the water. In some embodiments, the water does not comprise a detectable amount of an alkyl methanesulfonate. In some embodiments, the impurity is determined by high-performance liquid chromatography (HPLC).

In some embodiments, the purity of the methyl t-butyl ether is at least about 95% (weight %) and methyl t-butyl ether comprises no more than about 5% of an impurity (weight %) the methyl t-butyl ether. In some embodiments, the purity of the methyl t-butyl ether is at least about 97% (weight %) and methyl t-butyl ether comprises no more than about 3% of an impurity (weight %) the methyl t-butyl ether. In some embodiments, the purity of the methyl t-butyl ether is at least about 98% (weight %) and methyl t-butyl ether comprises no more than about 2% of an impurity (weight %) the methyl t-butyl ether. In some embodiments, the purity of the methyl t-butyl ether is at least about 99% (weight %) and methyl t-butyl ether comprises no more than about 1% of an impurity (weight %) the methyl t-butyl ether. In some embodiments, the methyl t-butyl ether does not comprise a detectable amount of an alkyl methanesulfonate. In some embodiments, the impurity is determined by high-performance liquid chromatography (HPLC). In some embodiments, the impurity is determined by gas chromatography (GC).

In some embodiments, Compound 1 does not comprise an impurity. In some embodiments Compound 1 comprises an impurity. In some embodiments, the impurity is an alkyl methanesulfonate. In some embodiments of the compounds of the invention, the alkyl methanesulfonate is methyl methanesulfonate, ethyl methanesulfonate, n-propyl methanesulfonate, or isopropyl methanesulfonate. In some embodiments, the impurity is a process by-product or a degradation product. In some embodiments, the impurity is Impurity A (N-(2-aminoethyl)-2-[(3-hydroxyphenyl)(4-methylphenyl)amino]-acetamide):

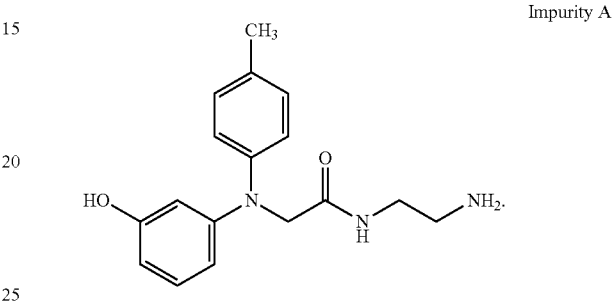

Impurity A

In some embodiments, the impurity is an Impurity A salt. In some embodiments, the impurity is an Impurity A methanesulfonate salt. In some embodiments, Impurity A is a by-product or degradation product.

In some embodiments, the impurity is Impurity B (2-chloromethyl-4,5-dihydro-1H-imidazole):

Impurity B

In some embodiments, Impurity B is a process byproduct. In some embodiments, the impurity is an Impurity B salt. In some embodiments, the impurity is an Impurity B methanesulfonate salt.

In some embodiments, the impurity is Impurity C (3-hydroxy-4'-methyldiphenylamine):

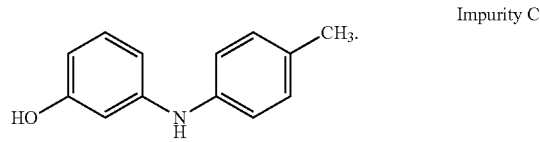 [SMILES: Cc1ccc(Nc2cccc(O)c2)cc1]

Impurity C

In some embodiments, Impurity C is a process by-product or degradation product. In some embodiments, Impurity C is a degradation product. In some embodiments, the impurity is an Impurity C salt. In some embodiments, the impurity is an Impurity C methanesulfonate salt. In some embodiments, the impurity is one or more of Impurity A, Impurity B, and Impurity C, or a salt thereof. In some embodiments, the salt is a methanesulfonic acid salt.

In some embodiments, the purity of Compound 1 is about 95.0% to 100% by weight, and Compound 1 comprises 0% to about 5.0% of an impurity by weight of Compound 1. In some embodiments, the purity of Compound 1 is about 98% to 100% by weight, and Compound 1 comprises 0% to about 2% of an impurity by weight of Compound 1. In some embodiments, the purity of Compound 1 is about 98%, about 98.5%, about 99%, about 99.5%, or 100% by weight, and Compound 1 comprises about 2%, about 1.5%, about 1%, about 0.5%, or 0%, respectively, of an impurity by weight of Compound 1. In some embodiments, the purity or the impurity are determined by high-performance liquid chromatography (HPLC). In some embodiments, the impurity is determined by titration.

In some embodiments, the purity of Compound 1 is at least about 98% by weight, and Compound 1 comprises no more than about 2% of an impurity by weight of Compound 1, as determined by GC. In some embodiments, the purity of Compound 1 is about 95.0% to 100% by weight, and comprises 0% to about 5.0% of an impurity by weight of Compound 1, as determined by GC. In some embodiments, the purity of Compound 1 is about 98% to 100% by weight, and Compound 1 comprises 0% to about 2% of an impurity by weight of Compound 1, as determined by GC. In some embodiments, the purity of Compound 1 is about 98%, about 98.5%, about 99%, about 99.5%, or 100% by weight, and Compound 1 comprises about 2%, about 1.5%, about 1%, about 0.5%, or 0% by weight of Compound 1, respectively, of an impurity as determined by GC. In some embodiments, Compound 1 comprises less than about 0.5% solvent as determined by GC. In some embodiments, Compound 1 comprises less than about 0.3% solvent as determined by GC.

In some embodiments, Compound 1 comprises less than 0.5% by weight of an impurity based on the weight of Compound 1. In some embodiments, Compound 1 comprises less than 0.5% impurity by weight, less than 0.4% impurity by weight, less than 0.3% impurity by weight, less than 0.2% impurity by weight, or less than 0.1% impurity by weight of Compound 1. In some embodiments, Compound 1 comprises no more than 0.5% impurity by weight of Compound 1. In some embodiments, Compound 1 comprises no more than 0.5% impurity by weight, no more than 0.4%, impurity by weight no more than 0.3% impurity by weight, no more than 0.2% impurity by weight, or no more than 0.1% impurity by weight of Compound 1. In some embodiments, the impurity is determined by high-performance liquid chromatography (HPLC). In some embodiments, the impurity is determined by titration.

In some embodiments, the impurity in Compound 1 is an alkyl methanesulfonate. In some embodiments of the compounds of the invention, the alkyl methanesulfonate is methyl methanesulfonate, ethyl methanesulfonate, n-propyl methanesulfonate, or isopropyl methanesulfonate.

In some embodiments, the impurity in Compound 1 is a process by-product or a degradation product.

In some embodiments, the impurity in Compound 1 is Impurity A (N-[2-aminoethyl)-2-[(3-hydroxyphenyl)(4-methylphenyl)amino]-acetamide). In some embodiments, the impurity is an Impurity A salt. In some embodiments, the impurity is an Impurity A methanesulfonate salt.

In some embodiments, Impurity A is a by-product or degradation product.

In some embodiments, the impurity in Compound 1 is Impurity B (2-chloromethyl-4,5-dihydro-1H-imidazole). In some embodiments, Impurity B is a process byproduct. In some embodiments, the impurity is an Impurity B salt. In some embodiments, the impurity is an Impurity B methanesulfonate salt.

In some embodiments, the impurity in Compound 1 is Impurity C (3-hydroxy-4'-methyldiphenylamine). In some embodiments, Impurity C is a process by-product or degradation product. In some embodiments, Impurity C is a degradation product. In some embodiments, the impurity is an Impurity C salt. In some embodiments, the impurity is an Impurity C methanesulfonate salt.

In some embodiments, the impurity in Compound 1 is one or more of Impurity A, Impurity B, and Impurity C, or a salt thereof. In some embodiments, the salt is a methanesulfonic acid salt.

In some embodiments, the impurity in Compound 1 is an alcohol solvent. In some embodiments, the alcohol solvent is methanol, ethanol, n-propanol, or isopropanol.

In some embodiments, the impurity in Compound 1 is toluene.

In some embodiments, the impurity in Compound 1 is acetone, ethyl acetate, or methyl t-butyl ether. In some embodiments, the impurity is water. In some embodiments of the compound of the invention, the impurity is a solvent.

In some embodiments, the purity of methanesulfonic acid is at least about 99% by weight, and methanesulfonic acid comprises no more than about 1% of an impurity by weight of the methanesulfonic acid. In some embodiments, the purity of methanesulfonic acid is about 95.0% to 100% by weight, and methanesulfonic acid comprises 0% to about 5.0% of an impurity by weight of the methanesulfonic acid. In some embodiments, the purity of methanesulfonic acid is about 98% to 100% by weight, and methanesulfonic acid comprises 0% to about 2% of an impurity by weight of the methanesulfonic acid. In some embodiments, the purity of methanesulfonic acid is about 98%, about 98.5%, about 99%, about 99.5%, or 100% by weight, and methanesulfonic acid comprises about 2%, about 1.5%, about 1%, about 0.5%, or 0%, respectively, of an impurity by weight of the methanesulfonic acid. In some embodiments, the purity or the impurity is determined by high-performance liquid chromatography (HPLC). In some embodiments, the impurity is determined by titration.

In some embodiments, the purity of methanesulfonic acid is at least about 99%, and methanesulfonic acid comprises no more than about 1% of an impurity by chromatographic area of the methanesulfonic acid peak, as determined by GC. In some embodiments, the purity of methanesulfonic acid is about 95.0% to 100%, and comprises 0% to about 5.0% of an impurity by chromatographic area of the methanesulfonic acid peak as determined by GC. In some embodiments, the purity of methanesulfonic acid is about 98% to 100%, and methanesulfonic acid comprises 0% to about 2% of an impurity by chromatographic area of the methanesulfonic acid peak, as determined by GC. In some embodiments, the purity of Compound 1 is about 98%, about 98.5%, about 99%, about 99.5%, or 100%, and methanesulfonic acid comprises about 2%, about 1.5%, about 1%, about 0.5%, or 0%, respectively, of an impurity by chromatographic area of the methanesulfonic acid peak as determined by GC. In some embodiments, methanesulfonic acid comprises less than about 0.5% solvent as determined by GC. In some embodiments, methanesulfonic acid comprises less than about 0.3% solvent as determined by GC.

In some embodiments, methanesulfonic acid comprises less than 1% or less than 0.5% of an impurity by weight of the methanesulfonic acid. In some embodiments, methanesulfonic acid comprises less than 1%, less than 0.9%, less than 0.8%, less than 0.7%, less than 0.6%, less than 0.5%, less than 0.4%, less than 0.3%, less than 0.2%, or less than 0.1% of an impurity by weight of the methanesulfonic acid. In some embodiments, methanesulfonic acid comprises no more than 1% or no more than 0.5% of an impurity by weight of the methanesulfonic acid. In some embodiments, methanesulfonic acid comprises no more than 1%, no more than 0.9%, no more than 0.8%, no more than 0.7%, no more than 0.6%, no more than 0.5%, no more than 0.4%, no more than 0.3%, no more than 0.2%, or no more than 0.1% of an impurity by weight of the methanesulfonic acid. In some embodiments, the impurity is determined by high-performance liquid chromatography (HPLC). In some embodiments, the impurity is determined by titration.

In some embodiments, the impurity in methanesulfonic acid is an alkyl methanesulfonate. In some embodiments of the compounds of the invention, the alkyl methanesulfonate is methyl methanesulfonate, ethyl methanesulfonate, n-propyl methanesulfonate, or isopropyl methanesulfonate.

In some embodiments, the impurity in methanesulfonic acid is an alcohol solvent. In some embodiments, the alcohol solvent is methanol, ethanol, n-propanol, or isopropanol.

In some embodiments, the impurity in methanesulfonic acid is toluene.

In some embodiments, the impurity in methanesulfonic acid is acetone, ethyl acetate, or methyl t-butyl ether. In some embodiments, the impurity is water. In some embodiments of the compound of the invention, the impurity is a solvent.

In some embodiments, the methods of the invention do not comprise subjecting the compound of the invention to further purification. In some embodiments, the methods of the invention do not comprise further purifying the compound of the invention.

Compounds of the Invention

In some embodiments, the compound of the invention is isolated phentolamine mesylate, filtered phentolamine mesylate or dried phentolamine mesylate.

In some embodiments, a compound of the invention is hygroscopic.

In some embodiments, a compound of the invention is stored or storable under inert gas. In some embodiments, inert gas is argon. In some embodiments, inert gas is nitrogen.

In some embodiments, a compound of the invention is hydroscopic and is stored or storable under an inert gas, e.g., nitrogen or argon.

In some embodiments, the compound of the invention is crystalline.

In some embodiments, the compound of the invention exhibits an X-ray powder diffraction (XRPD) pattern comprising a peak at about 6.87±0.2 degrees 2-theta, a peak at about 20.32±0.2 degrees 2-theta, and a peak at about 21.36±0.2 degrees 2-theta. In some embodiments, the compound of the invention exhibits an XRPD pattern further comprising a peak at about 18.86±0.2 degrees 2-theta and a peak at about 21.07±0.2 degrees 2-theta. In some embodiments, the compound of the invention exhibits an XRPD pattern further comprising a peak at about 11.65±0.2 degrees 2-theta, at about 13.15±0.2 degrees 2-theta, and a peak at about 20.85±0.2 degrees 2-theta. In some embodiments, the compound of the invention exhibits an XRPD pattern further comprising a peak at about 20.05±0.2 degrees 2-theta and a peak at about 23.87±0.2 degrees 2-theta. In some embodiments, the compound of the invention exhibits an XRPD pattern further comprising a peak at about 18.47±0.2 degrees 2-theta and a peak at about 19.38±0.2 degrees 2-theta. In some embodiments, the compound of the invention exhibits an XRPD pattern further comprising a peak at about 14.71±0.2 degrees 2-theta and a peak at about 22.22±0.2 degrees 2-theta.

In some embodiments, the compound of the invention exhibits an XRPD pattern comprising a peak at about 20.32±0.2 degrees 2-theta and a peak at about 21.36±0.2 degrees 2-theta. In some embodiments, the compound of the invention exhibits an XRPD pattern further comprising a peak at about 18.86±0.2 degrees 2-theta and a peak at about 13.15±0.2 degrees 2-theta. In some embodiments, the compound of the invention exhibits an XRPD pattern further comprising a peak at about 18.47±0.2 degrees 2-theta and a peak at about 20.05±0.2 degrees 2-theta. In some embodiments, the compound of the invention exhibits an XRPD pattern further comprising a peak at about 22.22±0.2 degrees 2-theta and a peak at about 23.24±0.2 degrees 2-theta. In some embodiments, the compound of the invention exhibits an XRPD pattern further comprising a peak at about 16.70±0.2 degrees 2-theta and a peak at about 21.70±0.2 degrees 2-theta. In some embodiments, the compound of the invention exhibits an XRPD pattern further comprising a peak at about 8.42±0.2 degrees 2-theta and a peak at about 8.53±0.2 degrees 2-theta.

In some embodiments, the compound of the invention exhibits an XRPD pattern comprising 1 peak, 2 peaks, 3 peaks, 4 peaks, 5 peaks, 6 peaks, 7 peaks, 8 peaks, 9 peaks, or 10 peaks of Table 1. In some embodiments, the compound of the invention exhibits an XRPD pattern comprising 1 peak, 2 peaks, 3 peaks, 4 peaks, 5 peaks, 6 peaks, 7 peaks, 8 peaks, 9 peaks, or 10 peaks of the following peaks: a peak at about 13.15±0.2 degrees 2-theta, a peak at about 16.70±0.2 degrees 2-theta, a peak at about 18.47±0.2 degrees 2-theta, a peak at about 18.86±0.2 degrees 2-theta, a peak at about 20.05±0.2 degrees 2-theta, a peak about 20.32±0.2 degrees 2-theta, a peak at about 21.36±0.2 degrees 2-theta, a peak at about 21.70±0.2 degrees 2-theta, a peak at about 22.22±0.2 degrees 2-theta and a peak at about 23.24±0.2 degrees 2-theta.

In some embodiments, the compound of the invention exhibits an XRPD pattern comprising a peak from Table 1 having a peak relative intensity (%) of greater than 70%. In some embodiments, the compound of the invention exhibits an XRPD pattern comprising a peak from Table 1 having a peak relative intensity (%) of greater than 50%. In some embodiments, the compound of the invention exhibits an XRPD pattern comprising a peak from Table 1 having a peak relative intensity (%) of greater than 30%.

In some embodiments, the compound of the invention exhibits an XRPD pattern comprising 1 peak, 2 peaks, 3 peaks, 4 peaks, 5 peaks, 6 peaks, 7 peaks, 8 peaks, 9 peaks, or 10 peaks of Table 3.

In some embodiments, the compound of the invention exhibits an XRPD pattern that is substantially the same as that depicted in FIG. 1.

Figure 3:
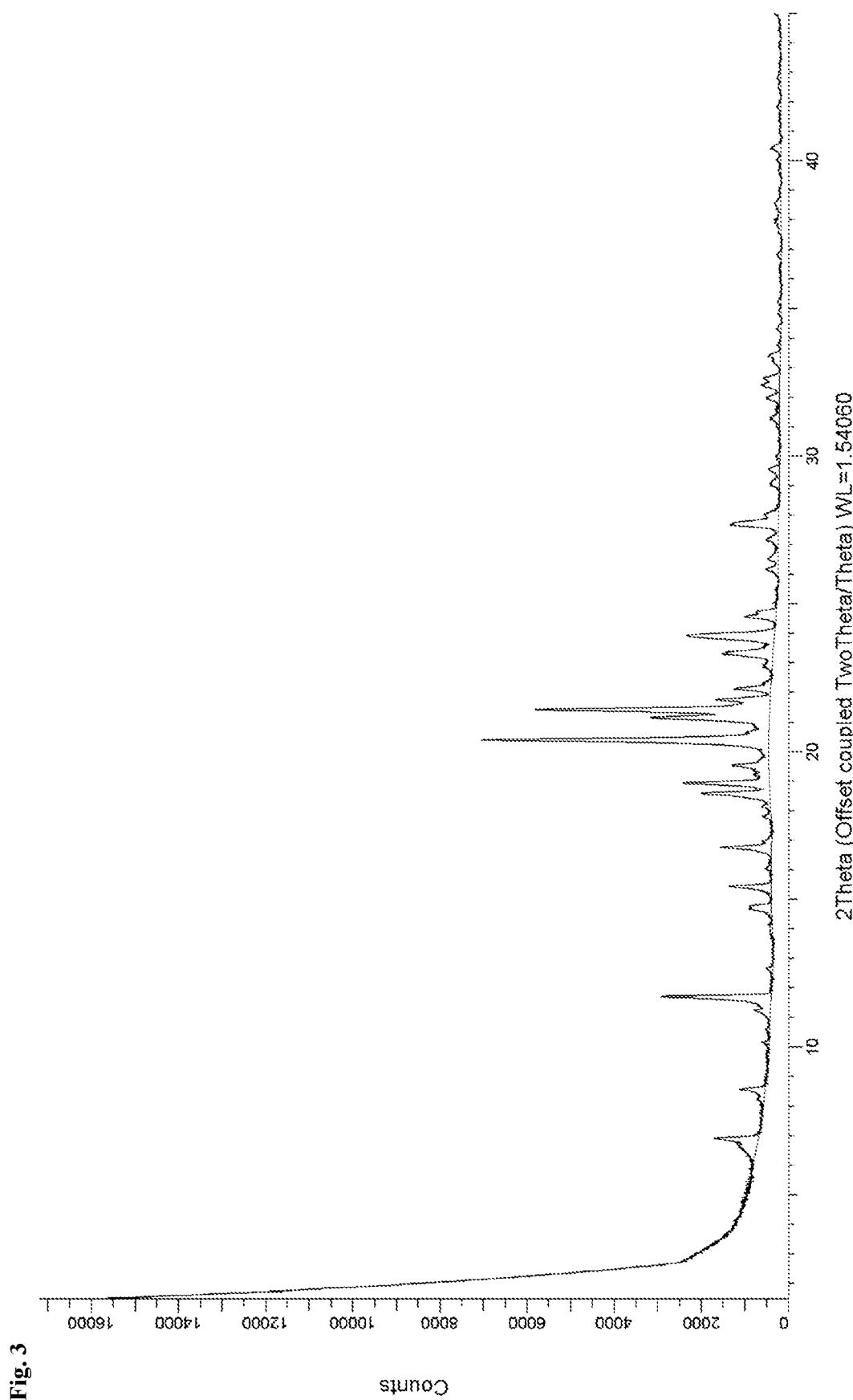
FIG. 3 shows an XRPD pattern of a phentolamine mesylate United States Pharmacopeia (USP) reference standard.

In some embodiments, the compound of the invention does not exhibit an XRPD pattern that is substantially the same as that depicted in FIG. 3.

In some embodiments, the compound of the invention comprises less than 5% of phentolamine mesylate exhibiting an XRPD pattern substantially the same as that depicted in FIG. 3, by weight of the compound of the invention. In some embodiments, the compound of the invention comprises less than 4% of phentolamine mesylate exhibiting an XRPD pattern substantially the same as that depicted in FIG. 3, by weight of the compound of the invention. In some embodiments, the compound of the invention comprises less than 2% of phentolamine mesylate exhibiting an XRPD pattern substantially the same as that depicted in in FIG. 3, by weight of the compound of the invention. In some embodiments, the compound of the invention comprises less than 1% of phentolamine mesylate exhibiting an XRPD pattern substantially the same as that depicted in FIG. 3, by weight of the compound of the invention. In some embodiments, the compound of the invention comprises less than 0.5% of phentolamine mesylate exhibiting an XRPD pattern substantially the same as that depicted in in FIG. 3, by weight of the compound of the invention.

In some embodiments, the compound of the invention exhibits a differential scanning calorimetry (DSC) thermogram comprising an endothermic peak having a peak maximum at about 180° C. In some embodiments, the compound of the invention exhibits a DSC thermogram comprising an endothermic peak that onsets at about 176° C.

In some embodiments, the compound of the invention exhibits a DSC thermogram comprising an endothermic peak having a peak maximum at about 120° C. In some embodiments, the compound of the invention exhibits a DSC thermogram comprising an endothermic peak that onsets at about 108° C.

In some embodiments, the compound of the invention exhibits a DSC thermogram comprising an endothermic peak having a peak maximum at about 133° C. In some embodiments, the compound of the invention exhibits a DSC thermogram comprising an endothermic peak that onsets at about 129° C.

In some embodiments, the compound of the invention exhibits a DSC thermogram comprising an endothermic peak having a peak maximum at about 120° C. and a peak maximum at about at about 180° C. In some embodiments, the compound of the invention exhibits a DSC thermogram comprising an endothermic peak that onsets at about 108° C. and an endothermic peak that onsets at about 176° C.

In some embodiments, the compound of the invention exhibits a DSC thermogram comprising an exothermic peak having a peak maximum between about 245° C. and about 250° C.

Figure 2:
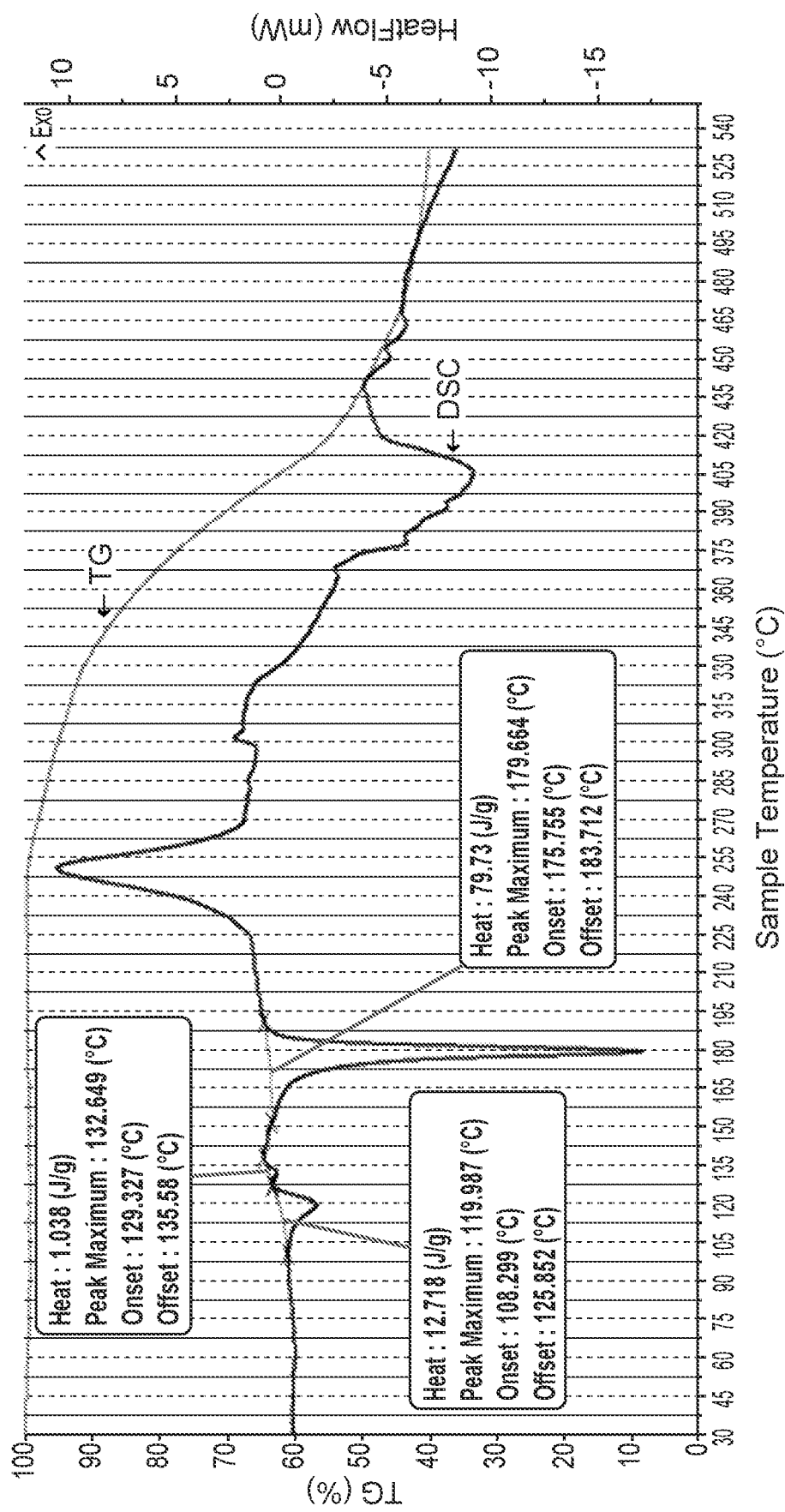
FIG. 2 shows an overlay of a thermo-gravimetric (TG) thermogram and a differential scanning calorimetry (DSC) thermogram of phentolamine mesylate obtained as described in Example 2.

In some embodiments, the compound of the invention exhibits a DSC thermogram that is substantially the same as that depicted in FIG. 2.

In some embodiments, the compound of the invention exhibits a thermo-gravimetric (TG) thermogram that is substantially the same as that depicted in FIG. 2.

Figure 4:
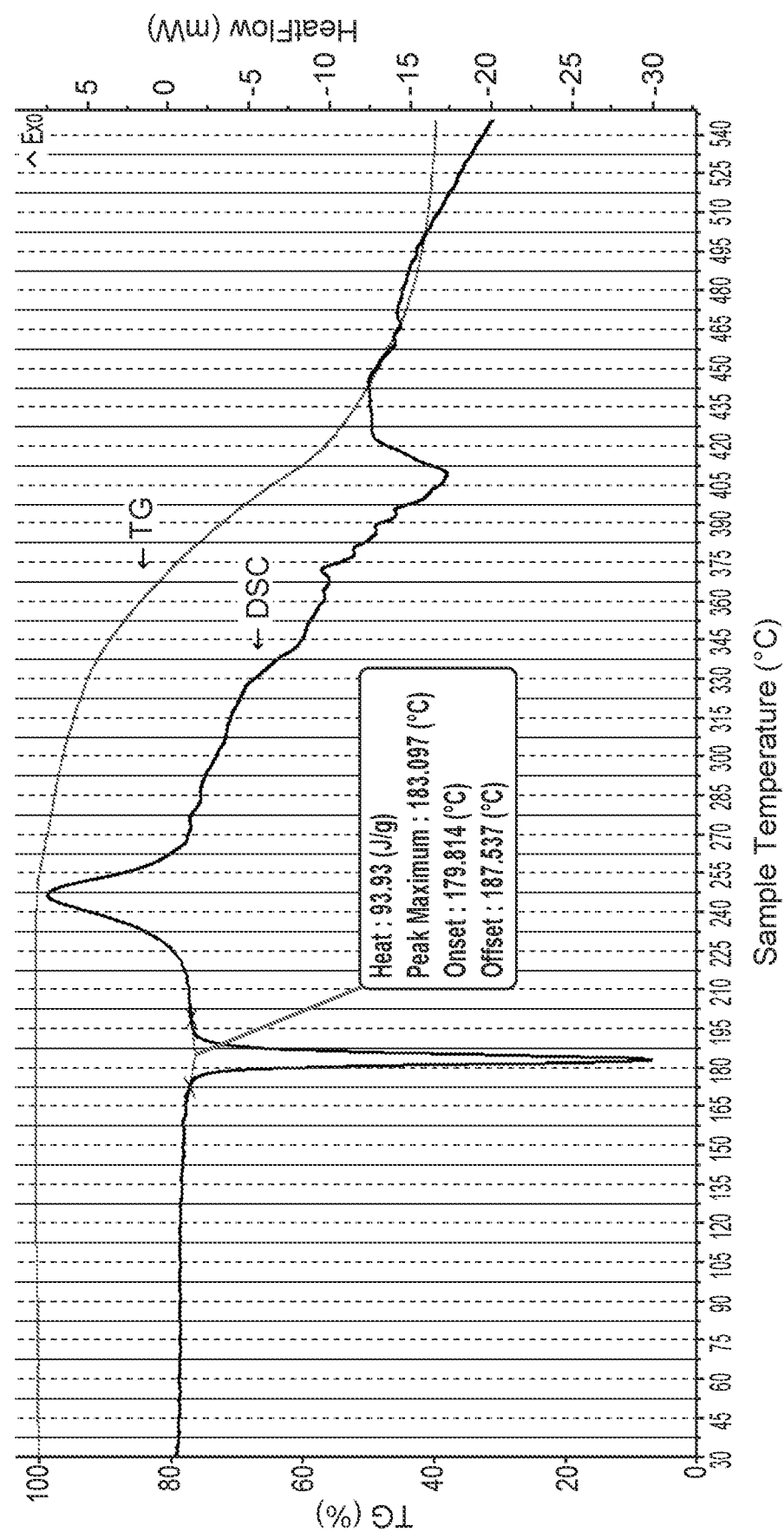
FIG. 4 shows an overlay of a TG thermogram of a phentolamine mesylate USP reference standard and a DSC thermogram of phentolamine mesylate USP reference standard.

In some embodiments, the compound of the invention does not exhibit a DSC thermogram that is substantially the same as that depicted in FIG. 4.

In some embodiments, the compound of the invention does not exhibit a TG thermogram that is substantially the same as that depicted in FIG. 4.

In some embodiments, the compound of the invention comprises less than about 20% of amorphous phentolamine mesylate by weight or mole of the compound of the invention. In some embodiments, the compound of the invention comprises less than about 15% of amorphous phentolamine mesylate by weight or mole of the compound of the invention. In some embodiments, the compound of the invention comprises less than about 10% of amorphous phentolamine mesylate by weight or mole of the compound of the invention. In some embodiments, the compound of the invention comprises less than about 5% of amorphous phentolamine mesylate by weight or mole of the compound of the invention.

In some embodiments, the compound of the invention has a molar ratio of crystalline phentolamine mesylate to amorphous phentolamine mesylate of at least 4:1. In some embodiments, the compound of the invention has a molar ratio of crystalline phentolamine mesylate to amorphous phentolamine mesylate of at least 5:1. In some embodiments, the compound of the invention has a molar ratio of crystalline phentolamine mesylate to amorphous phentolamine mesylate of at least 17:3. In some embodiments, the compound of the invention has a molar ratio of crystalline phentolamine mesylate to amorphous phentolamine mesylate of at least 6:1. In some embodiments, the compound of the invention has a molar ratio of crystalline phentolamine mesylate to amorphous phentolamine mesylate of at least 7:1. In some embodiments, the compound of the invention has a molar ratio of crystalline phentolamine mesylate to amorphous phentolamine mesylate of at least 8:1. In some embodiments, the compound of the invention has a molar ratio of crystalline phentolamine mesylate to amorphous phentolamine mesylate of at least 9:1. In some embodiments, the compound of the invention has a molar ratio of crystalline phentolamine mesylate to amorphous phentolamine mesylate of at least 10:1. In some embodiments, the compound of the invention has a molar ratio of crystalline phentolamine mesylate to amorphous phentolamine mesylate of at least 11:1. In some embodiments, the compound of the invention has a molar ratio of crystalline phentolamine mesylate to amorphous phentolamine mesylate of at least 23:2. In some embodiments, the compound of the invention has a molar ratio of crystalline phentolamine mesylate to amorphous phentolamine mesylate of at least 12:1. In some embodiments, the compound of the invention has a molar ratio of crystalline phentolamine mesylate to amorphous phentolamine mesylate of at least 13:1. In some embodiments, the compound of the invention has a molar ratio of crystalline phentolamine mesylate to amorphous phentolamine mesylate of at least 93:7. In some embodiments, the compound of the invention has a molar ratio of crystalline phentolamine mesylate to amorphous phentolamine mesylate of at least 14:1. In some embodiments, the compound of the invention has a molar ratio of crystalline phentolamine mesylate to amorphous phentolamine mesylate of at least 15:1. In some embodiments, the compound of the invention has a molar ratio of crystalline phentolamine mesylate to amorphous phentolamine mesylate of at least 16:1. In some embodiments, the compound of the invention has a molar ratio of crystalline phentolamine mesylate to amorphous phentolamine mesylate of at least 17:1. In some embodiments, the compound of the invention has a molar ratio of crystalline phentolamine mesylate to amorphous phentolamine mesylate of at least 18:1. In some embodiments, the compound of the invention has a molar ratio of crystalline phentolamine mesylate to amorphous phentolamine mesylate of at least 19:1. In some embodiments, the compound of the invention has a molar ratio of crystalline phentolamine mesylate to amorphous phentolamine mesylate of at least 20:1.

The present invention further provides a compound of invention that is at least about 98% (weight %) of the compound of the invention, and a compound of the invention comprises no more than about 2% of an impurity (weight %) of the compound of the invention. In some embodiments, the purity of a compound of the invention is about 95.0% to 100%, and a compound of the invention comprises 0% to about 5% of an impurity by weight of the compound of the invention. In some embodiments, the purity of a compound of the invention is about 98% to 100%, and a compound of the invention comprises 0% to about 2% of an impurity by weight of the compound of the invention. In some embodiments, the purity of a compound of the invention is about 98%, about 98.5%, about 99%, about 99.5%, or 100%, and a compound of the invention comprises about 2%, about 1.5%, about 1%, about 0.5%, or 0%, respectively, of an impurity by weight of the compound of the invention, after drying. In some embodiments, the purity of a compound of the invention is about 99.5%, about 99.9%, or about 99.95%, and a compound of the invention comprises about 0.5%, about 0.1%, or about 0.05%, respectively, of an impurity by weight of the compound of the invention, after drying. In some embodiments, the purity of a compound of the invention is about 98%, about 98.5%, about 99%, about 99.5%, or 100%, and a compound of the invention comprises about 2%, about 1.5%, about 1%, about 0.5%, or 0%, respectively, of an impurity by weight of the compound of the invention, after drying by rotary evaporator. In some embodiments, the purity of a compound of the invention is about 99.5%, about 99.9%, or about 99.95%, and a compound of the invention comprises about 0.5%, about 0.1%, or about 0.05%, respectively, of an impurity by weight of the compound of the invention, after drying by rotary evaporator. In some embodiments, the purity of a compound of the invention is about 98%, about 98.5%, about 99%, about 99.5%, or 100%, and a compound of the invention comprises about 2%, about 1.5%, about 1%, about 0.5%, or 0%, respectively, of an impurity by weight of the compound of the invention, after lyophilizing. In some embodiments, the impurity is determined by high-performance liquid chromatography (HPLC). In some embodiments, the impurity is determined by titration.

In some embodiments, the compound of invention comprises less than about 1% of an impurity by weight of the compound of the invention. In some embodiments, the compound of invention comprises less than about 0.5% of an impurity by weight of the compound of the invention. In some embodiments, the compound of invention comprises less than about 1%, less than about 0.9%, less than about 0.8%, less than about 0.7%, less than about 0.6%, less than about 0.5%, less than about 0.4%, less than about 0.3%, or less than about 0.2% of an impurity by weight of the compound of the invention.

In some embodiments, the purity determination of a compound of the invention by HPLC comprises comparing a compound of the invention to a reference sample of phentolamine mesylate having a certified purity. In some embodiments, the purity of a compound of the invention is determined by HPLC as being about 95% to about 102%, in some embodiments, about 95% to about 100%. In some embodiments, the purity of a compound of the invention determined by HPLC accounts for only impurity that can be detected by the HPLC method used. In some embodiments, the purity determined by HPLC of a compound of the invention does not account for presence of solvent, if any.

In some embodiments, the purity of a compound of the invention is determined by HPLC using a mobile phase that is 0.5 g/L ammonium acetate in a water:acetonitrile (67:33) solution. In some embodiments, the HPLC method used in determining the purity of a compound of the invention comprises using a detector set at about 220 nm to about 230 nm.

In some embodiments, the purity of a compound of the invention is at least about 98%, and a compound of the invention comprises no more than about 2% of an impurity by chromatographic area of the peak of the compound of the invention, as determined by gas chromatography (GC). In some embodiments, the purity of a compound of the invention is about 95.0% to 100%, and a compound of the invention comprises no more than 0% to about 5.0% of an impurity by chromatographic area of the peak of the compound of the invention, as determined by GC. In some embodiments, the purity of a compound of the invention is about 98% to 100%, and a compound of the invention comprises 0% to about 2% of an impurity by chromatographic area of the peak of the compound of the invention, as determined by GC. In some embodiments, the GC method used in determining the purity of a compound of the invention comprises United States Pharmacopeia (USP) Method <467>. In some embodiments, a compound of the invention comprises less than about 0.5% solvent as determined by GC. In some embodiments, a compound of the invention comprises less than about 0.3% solvent as determined by GC. In some embodiments, a compound of the invention comprises less than about 0.5% or less than about 0.3% solvent as determined by GC, after drying. In some embodiments, a compound of the invention comprises less than about 0.5% or less than about 0.3% solvent as determined by GC, after lyophilizing.

In some embodiments, a compound of the invention comprises less than 1.5% of an impurity by weight of the compound of the invention. In some embodiments, a compound of the invention comprises less than 1% of an impurity by weight of the compound of the invention. In some embodiments, a compound of the invention comprises less than 0.5% of an impurity by weight of the compound of the invention. In some embodiments, the impurity is Compound 1. In some embodiments, the impurity is determined by high-performance liquid chromatography (HPLC). In some embodiments, the impurity is determined by titration.

In some embodiments, a compound of the invention does not comprise a detectable amount of an alkyl methanesulfonate. In some embodiments the detectable amount is detectable by GC, HPLC, or titration.

In some embodiments, the alkyl methanesulfonate is methyl methanesulfonate, ethyl methanesulfonate, n-propyl methanesulfonate, or isopropyl methanesulfonate.

In some embodiments, a compound of the invention comprises less than about 8% water by weight as determined by Karl Fischer titration. In some embodiments, a compound of the invention comprises less than about 6% water by weight of the compound of the invention, as determined by Karl Fischer titration. In some embodiments, a compound of the invention comprises less than about 2% water by weight as determined by Karl Fischer titration. In some embodiments, a compound of the invention comprises less than about 1% water by weight of the compound of the invention, as determined by Karl Fischer titration. In some embodiments, a compound of the invention comprises less than about 0.5% water by weight of the compound of the invention, as determined by Karl Fischer titration. In some embodiments, a compound of the invention comprises less than about 8%, less than about 7.5%, less than about 7%, less than about 6.5%, less than about 6%, less than about 5.5%, less than about 5%, less than about 4.5%, less than about 4%, less than about 3.5%, less than about 3%, less than about 2.5%, less than about 2%, less than about 1.5%, less than about 1%, or less than about 0.5% water by weight of the compound of the invention, as determined by Karl Fischer titration.

In some embodiments, a compound of the invention comprises less than about 8% or less than about 6% water by weight of the compound of the invention, as determined by Karl Fischer titration, after drying. In some embodiments, a compound of the invention comprises less than about 8% or less than about 6% water by weight of the compound of the invention, as determined by Karl Fischer titration, after drying by rotary evaporator.

In some embodiments, a compound of the invention comprises less than about 2% or less than about 1% water by weight of the compound of the invention, as determined by Karl Fischer titration, after drying. In some embodiments, a compound of the invention comprises less than about 2% or less than about 1% water by weight of the compound of the invention, as determined by Karl Fischer titration, after lyophilizing.

The present invention further provides a compound of invention that is obtained or obtainable as described in Example 1. In some embodiments, the compound of the invention that is obtained or obtainable as described in Example 1 is a crystalline phentolamine mesylate. In some embodiments, the compound of the invention is more than 99% pure without subjecting it to further purification.

The present invention further provides a compound of invention that is obtained or obtainable as described in Example 2. In some embodiments, the compound of the invention that is obtained or obtainable as described in Example 2 is a crystalline phentolamine mesylate. In some embodiments, the compound of the invention is more than 99% pure without subjecting it to further purification.

The present invention further provides a compound of invention that is made or makable by a synthesis method of the invention.

In some embodiments, a compound of invention does not comprise an impurity. In some embodiments, the compound of the invention does not comprise a detectable amount of an impurity. In some embodiments, the isolated phentolamine mesylate, filtered phentolamine mesylate, or dried phentolamine mesylate does not comprise a detectable amount of an impurity. In some embodiments, the compound of the invention is more than 99% pure without subjecting it to further purification. In some embodiments, the isolated phentolamine mesylate, filtered phentolamine mesylate, or dried phentolamine mesylate is more than 99% pure without subjecting it to further purification.

The present invention further provides phentolamine mesylate comprising less than 1% of an impurity by weight of the phentolamine mesylate. In some embodiments, the phentolamine mesylate comprises less than 0.5% of the impurity by weight of the phentolamine mesylate. In some embodiments, the phentolamine mesylate comprises less than 0.1% of the impurity by weight of the phentolamine mesylate. In some embodiments, the phentolamine mesylate comprises less than 1% of an impurity by weight, less than 0.9% of an impurity by weight, less than 0.8% of an impurity by weight, less than 0.7% of an impurity by weight, less than 0.6% of an impurity by weight, less than 0.5% of an impurity by weight, less than 0.4% of an impurity by weight, less than 0.3% of an impurity by weight, less than 0.2% of an impurity by weight, less than 0.1% of an impurity by weight, or less than 0.05% of an impurity by weight of the phentolamine mesylate. In some embodiments, the phentolamine mesylate is an isolated phentolamine mesylate, a filtered phentolamine mesylate, or a dried phentolamine mesylate that is not subjected to further purification. In some embodiments, the phentolamine mesylate is a dried phentolamine mesylate that is not subjected to further purification.

The present invention further provides phentolamine mesylate comprising water in the range of 0% by weight to about 6% by weight of the phentolamine mesylate and comprises less than 1% of an impurity by weight of the phentolamine mesylate. In some embodiments, the phentolamine mesylate comprises less than 0.5% of the impurity by weight of the phentolamine mesylate. In some embodiments, the phentolamine mesylate comprises less than 0.3% of the impurity by weight of the phentolamine mesylate. In some embodiments, the phentolamine mesylate comprises less than 0.1% of the impurity by weight of the phentolamine mesylate. In some embodiments, the phentolamine mesylate comprises less than 1% of the impurity by weight, less than 0.9% of the impurity by weight, less than 0.8% of the impurity by weight, less than 0.7% of the impurity by weight, less than 0.6% of the impurity by weight, less than 0.5% of the impurity by weight, less than 0.4% of the impurity by weight, less than 0.3% of the impurity by weight, less than 0.2% of the impurity by weight, less than 0.1% of the impurity by weight, or less than 0.05% of the impurity by weight of the phentolamine mesylate. In some embodiments, the phentolamine mesylate comprises 0% water by weight to about 3% water by weight of the phentolamine mesylate. In some embodiments, the phentolamine mesylate comprises 0% water by weight to about 2% water by weight of the phentolamine mesylate. In some embodiments, the phentolamine mesylate comprises 0% water by weight to about 1.5% water by weight of the phentolamine mesylate. In some embodiments, the phentolamine mesylate comprises 0% water by weight to about 6% water by weight of the phentolamine mesylate and comprises less than 0.5% of an impurity by weight of the phentolamine mesylate. In some embodiments, the phentolamine mesylate comprises 0% water by weight to about 6% water by weight of the phentolamine mesylate and comprises less than 0.3% of an impurity by weight of the phentolamine mesylate. In some embodiments, the phentolamine mesylate comprises 0% water by weight to about 3% water by weight of the phentolamine mesylate and comprises less than 0.5% of the impurity by weight of the phentolamine mesylate. In some embodiments, the phentolamine mesylate comprises 0% water by weight to about 2% water by weight of the phentolamine mesylate and comprises less than 0.5% of an impurity by weight of the phentolamine mesylate. In some embodiments, the phentolamine mesylate comprises 0% water by weight to about 2% water by weight of the phentolamine mesylate and comprises less than 0.1% of an impurity by weight of the phentolamine mesylate.

In some embodiments, the impurity is Compound 1.

In some embodiments, the impurity is an alkyl methanesulfonate. In some embodiments of a compounds of the invention, the alkyl methanesulfonate is methyl methanesulfonate, ethyl methanesulfonate, n-propyl methanesulfonate, or isopropyl methanesulfonate.

In some embodiments, the impurity is a process by-product or a degradation product.

In some embodiments, the impurity is Impurity A (N-(2-aminoethyl)-2-[(3-hydroxyphenyl)(4-methylphenyl) amino]-acetamide).

In some embodiments, the impurity is an Impurity A salt. In some embodiments, the impurity is an Impurity A methanesulfonate salt.

In some embodiments, Impurity A is a process by-product or degradation product.

In some embodiments, the impurity is Impurity B (2-chloromethyl-4,5-dihydro-1H-imidazole). In some embodiments, the impurity is an Impurity B salt. In some embodiments, the impurity is an Impurity B methanesulfonate salt.

In some embodiments, Impurity B is a process by-product or degradation product.

In some embodiments, the impurity is Impurity C (3-hydroxy-4'-methyldiphenylamine). In some embodiments, the impurity is an Impurity C salt. In some embodiments, the impurity is an Impurity C methanesulfonate salt.

In some embodiments, Impurity C is a process by-product. In some embodiments, Impurity C is a degradation product.

In some embodiments, the impurity is one or more of Impurity A, Impurity B, and Impurity C, or a salt thereof. In some embodiments, the salt is a methanesulfonic acid salt.

In some embodiments of the compounds of the invention, the impurity is an alcohol solvent. In some embodiments of the compounds of the invention, the alcohol solvent is methanol, ethanol, n-propanol, or isopropanol.

In some embodiments of the compounds of the invention, the impurity is toluene.

In some embodiments of the compounds of the invention, the isolated phentolamine mesylate, filtered phentolamine mesylate, or dried phentolamine mesylate comprises toluene in an amount of less than 890 ppm as determined by GC. In some embodiments of the compounds of the invention, the isolated phentolamine mesylate, filtered phentolamine mesylate, or dried phentolamine mesylate comprises toluene in an amount of less than 5 ppm, less than 4 ppm, less than 3 ppm, less than 2 ppm, or less than 1 ppm as determined by GC. In some embodiments, the isolated phentolamine mesylate, filtered phentolamine mesylate, or dried phentolamine mesylate does not comprise toluene.

In some embodiments of the compounds of the invention, the isolated phentolamine mesylate, filtered phentolamine mesylate, or dried phentolamine mesylate comprises acetone in an amount of less than 5000 ppm as determined by GC. In some embodiments, the isolated phentolamine mesylate, filtered phentolamine mesylate, or dried phentolamine mesylate comprises acetone in an amount of less than 1000 ppm, less than 900 ppm, less than 800 ppm, or less than 700 ppm as determined by GC.

In some embodiments of the compounds of the invention, the isolated phentolamine mesylate, filtered phentolamine mesylate, or dried phentolamine mesylate comprises ethyl acetate in an amount of less than 5000 ppm as determined by GC. In some embodiments, the isolated phentolamine mesylate, filtered phentolamine mesylate, or dried phentolamine mesylate comprises ethyl acetate in an amount of less than 100 ppm, less than 90 ppm, less than 80 ppm, less than 70 ppm, less than 60 ppm, less than 50 ppm, less than 40 ppm, or less than 30 ppm as determined by GC.

In some embodiments of the compounds of the invention, the isolated phentolamine mesylate, filtered phentolamine mesylate, or dried phentolamine mesylate comprises methyl t-butyl ether in an amount of less than 5000 ppm as determined by GC. In some embodiments, the isolated phentolamine mesylate, filtered phentolamine mesylate, or dried phentolamine mesylate comprises methyl t-butyl ether in an amount of less than 200 ppm, less than 180 ppm, less than 160 ppm, less than 140 ppm, less than 120 ppm, or less than 110 ppm as determined by GC.

In some embodiments of the compounds of the invention, the impurity is water.

In some embodiments, the isolated phentolamine mesylate, filtered phentolamine mesylate, or dried phentolamine mesylate comprises an impurity that is no more than 5% by weight of the phentolamine mesylate.

In some embodiments, the isolated phentolamine mesylate, filtered phentolamine mesylate, or dried phentolamine mesylate comprises an impurity that is no more than 4.5%, no more than 4%, no more than 3.5%, no more than 3%, no more than 2.5%, no more than 2%, no more than 1.5%, or no more than 1% by weight of the phentolamine mesylate.

In some embodiments, the impurity is Compound 1.

In some embodiments, the impurity is an alkyl methanesulfonate. In some embodiments of the compounds of the invention, the alkyl methanesulfonate is methyl methanesulfonate, ethyl methanesulfonate, n-propyl methanesulfonate, or isopropyl methanesulfonate.

In some embodiments, the impurity is a process by-product or a degradation product.

In some embodiments, the impurity is Impurity A (N-(2-aminoethyl)-2-[(3-hydroxyphenyl)(4-methylphenyl) amino]-acetamide). In some embodiments, the impurity is an Impurity A salt. In some embodiments, the impurity is an Impurity A methanesulfonate salt.

In some embodiments, Impurity A is a process by-product or degradation product.

In some embodiments, the impurity is Impurity B (2-chloromethyl-4,5-dihydro-1H-imidazole). In some embodiments, the impurity is an Impurity B salt. In some embodiments, the impurity is an Impurity B methanesulfonate salt. In some embodiments, Impurity B is a process by-product or degradation product.

In some embodiments, the impurity is Impurity C (3-hydroxy-4'-methyldiphenylamine). In some embodiments, the impurity is an Impurity C salt. In some embodiments, the impurity is an Impurity C methanesulfonate salt. In some embodiments, Impurity C is a process by-product. In some embodiments, Impurity C is a degradation product.

In some embodiments, the impurity is one or more of Impurity A, Impurity B, and Impurity C, or a salt thereof. In some embodiments, the salt is a methanesulfonic acid salt.

In some embodiments of the compounds of the invention, the impurity is an alcohol solvent. In some embodiments of the compounds of the invention, the alcohol solvent is methanol, ethanol, n-propanol, or isopropanol.

In some embodiments of the compounds of the invention, the impurity is toluene.

In some embodiments of the compounds of the invention, the isolated phentolamine mesylate, filtered phentolamine mesylate, or dried phentolamine mesylate comprises toluene in an amount of no more than 890 ppm as determined by GC. In some embodiments of the compounds of the invention, the isolated phentolamine mesylate, filtered phentolamine mesylate, or dried phentolamine mesylate comprises toluene in an amount of no more than 5 ppm, no more than 4 ppm, no more than 3 ppm, no more than 2 ppm, or no more than 1 ppm as determined by GC.

In some embodiments of the compounds of the invention, the isolated phentolamine mesylate, filtered phentolamine mesylate, or dried phentolamine mesylate comprises acetone in an amount of no more than 5000 ppm as determined by GC. In some embodiments, the isolated phentolamine mesylate, filtered phentolamine mesylate, or dried phentolamine mesylate comprises acetone in an amount of no more than 1000 ppm, no more than 900 ppm, no more than 800 ppm, or no more than 700 ppm as determined by GC.

In some embodiments of the compounds of the invention, the isolated phentolamine mesylate, filtered phentolamine mesylate, or dried phentolamine mesylate comprises ethyl acetate in an amount of no more than 5000 ppm as determined by GC. In some embodiments, the isolated phentolamine mesylate, filtered phentolamine mesylate, or dried phentolamine mesylate comprises ethyl acetate in an amount of no more than 100 ppm, no more than 90 ppm, no more than 80 ppm, no more than 70 ppm, no more than 60 ppm, no more than 50 ppm, no more than 40 ppm, or no more than 30 ppm as determined by GC.

In some embodiments of the compounds of the invention, the isolated phentolamine mesylate, filtered phentolamine mesylate, or dried phentolamine mesylate comprises methyl t-butyl ether in an amount of no more than 5000 ppm as determined by GC. In some embodiments, the isolated phentolamine mesylate, filtered phentolamine mesylate, or dried phentolamine mesylate comprises methyl t-butyl ether in an amount of no more than 200 ppm, no more than 180 ppm, no more than 160 ppm, no more than 140 ppm, no more than 120 ppm, or no more than 110 ppm as determined by GC.

In some embodiments, the purity of the isolated phentolamine mesylate, filtered phentolamine mesylate, or dried phentolamine mesylate is at least about 98% (weight %), and comprises no more than about 2% of an impurity by weight of the phentolamine mesylate. In some embodiments, the purity or the impurity are determined by high-performance liquid chromatography (HPLC). In some embodiments, the impurity is determined by titration.

In some embodiments, the purity of the isolated phentolamine mesylate, filtered phentolamine mesylate, or dried phentolamine mesylate is about 95.0% to 100% by weight, and the isolated phentolamine mesylate, filtered phentolamine mesylate, or dried phentolamine mesylate comprises 0% to about 5.0% of an impurity by weight of the phentolamine mesylate. In some embodiments, the purity of the isolated phentolamine mesylate, filtered phentolamine mesylate, or dried phentolamine mesylate is about 98% to 100% by weight, and the isolated phentolamine mesylate, filtered phentolamine mesylate, or dried phentolamine mesylate comprises 0% to about 2% of an impurity by weight of the phentolamine mesylate. In some embodiments, the purity of the isolated phentolamine mesylate, filtered phentolamine mesylate, or dried phentolamine mesylate is about 98%, about 98.5%, about 99%, about 99.5%, or 100% by weight, and the isolated phentolamine mesylate, filtered phentolamine mesylate, or dried phentolamine mesylate comprises about 2%, about 1.5%, about 1%, about 0.5%, or 0%, respectively, of an impurity by weight of the phentolamine mesylate. In some embodiments, the purity or the impurity are determined by high-performance liquid chromatography (HPLC). In some embodiments, the impurity is determined by titration.

In some embodiments of the compounds of the invention, the purity of the isolated phentolamine mesylate, filtered phentolamine mesylate, or dried phentolamine mesylate is at least about 98%, and the isolated phentolamine mesylate, filtered phentolamine mesylate, or dried phentolamine mesylate comprises no more than about 2% of an impurity by chromatographic area of the peak of the compound of the invention, as determined by GC. In some embodiments, the purity of the isolated phentolamine mesylate, filtered phentolamine mesylate, or dried phentolamine mesylate is about 95.0% to 100%, and comprises 0% to about 5.0% of an impurity by chromatographic area of the peak of the compound of the invention, as determined by GC. In some embodiments, the purity of the isolated phentolamine mesylate, filtered phentolamine mesylate, or dried phentolamine mesylate is about 98% to 100%, and the isolated phentolamine mesylate, filtered phentolamine mesylate, or dried phentolamine mesylate comprises 0% to about 2% of an impurity by chromatographic area of the peak of the compound of the invention, as determined by GC. In some embodiments, the purity of the isolated phentolamine mesylate, filtered phentolamine mesylate, or dried phentolamine mesylate is about 98%, about 98.5%, about 99%, about 99.5%, or 100%, and the isolated phentolamine mesylate, filtered phentolamine mesylate, or dried phentolamine mesylate comprises about 2%, about 1.5%, about 1%, about 0.5%, or 0%, respectively, of an impurity by chromatographic area of the peak of the compound of the invention as determined by GC. In some embodiments, the isolated phentolamine mesylate, filtered phentolamine mesylate, or dried phentolamine mesylate comprises less than about 0.5% solvent as determined by GC. In some embodiments, the isolated phentolamine mesylate, filtered phentolamine mesylate, or dried phentolamine mesylate comprises less than about 0.3% solvent as determined by GC.

In some embodiments of the compounds of the invention, the isolated phentolamine mesylate, filtered phentolamine mesylate, or dried phentolamine mesylate comprises less than 1.5% of an impurity by weight of the compound of the invention. In some embodiments, the isolated phentolamine mesylate, filtered phentolamine mesylate, or dried phentolamine mesylate comprises less than 1% of an impurity by weight of the compound of the invention. In some embodiments, the isolated phentolamine mesylate, filtered phentolamine mesylate, or dried phentolamine mesylate comprises less than 0.5% of an impurity by weight of the compound of the invention. In some embodiments, the impurity is Compound 1. In some embodiments, the impurity is one or more of Impurity A, Impurity B, and Impurity C, or a salt thereof. In some embodiments, the salt is a methanesulfonic acid salt. In some embodiments, the impurity is determined by high-performance liquid chromatography (HPLC). In some embodiments, the impurity is determined by titration.

In some embodiments of the compounds of the invention, the isolated phentolamine mesylate, filtered phentolamine mesylate, or dried phentolamine mesylate comprises less than about 8% water by weight of the compound of the invention, as determined by Karl Fischer titration. In some embodiments, the isolated phentolamine mesylate, filtered phentolamine mesylate, or dried phentolamine mesylate comprises less than about 6% water by weight of the compound of the invention, as determined by Karl Fischer titration. In some embodiments, the isolated phentolamine mesylate, filtered phentolamine mesylate, or dried phentolamine mesylate comprises less than about 1% water by weight of the compound of the invention, as determined by Karl Fischer titration. In some embodiments, the isolated phentolamine mesylate, filtered phentolamine mesylate, or dried phentolamine mesylate comprises less than about 8%, less than about 7.5%, less than about 7%, less than about 6.5%, less than about 6%, less than about 5.5%, less than about 5%, less than about 4.5%, less than about 4%, less than about 3.5%, less than about 3%, less than about 2.5%, less than about 2%, less than about 1.5%, less than about 1%, or less than about 0.5% water by weight of the compound of the invention, as determined by Karl Fischer titration.

In some embodiments, the invention provides compositions comprising a compound of the invention and an impurity, wherein the impurity is present in the composition in an amount of no more than 0.5% by weight, mole or volume of the composition. In some embodiments, the invention provides compositions comprising the compound of the invention and an impurity, wherein the impurity is present in the composition in an amount of no more than 0.4%, no more than 0.3%, no more than 0.2%, or no more than 0.1% of the mixture, by weight, mole or volume of the composition.

In some embodiments, the impurity is Compound 1.

In some embodiments, the impurity is an alkyl methanesulfonate. In some embodiments of the compounds of the invention, the alkyl methanesulfonate is methyl methanesulfonate, ethyl methanesulfonate, n-propyl methanesulfonate, or isopropyl methanesulfonate.

In some embodiments, the impurity is a process by-product or a degradation product.

In some embodiments, the impurity is Impurity A (N-(2-aminoethyl)-2-[(3-hydroxyphenyl)(4-methylphenyl) amino]-acetamide). In some embodiments, the impurity is an Impurity A salt. In some embodiments, the impurity is an Impurity A methanesulfonate salt.

In some embodiments, Impurity A is a by-product or degradation product.

In some embodiments, the impurity is Impurity B (2-chloromethyl-4,5-dihydro-1H-imidazole). In some embodiments, Impurity B is a process byproduct. In some embodiments, the impurity is an Impurity B salt. In some embodiments, the impurity is an Impurity B methanesulfonate salt.

In some embodiments, the impurity is Impurity C (3-hydroxy-4'-methyldiphenylamine). In some embodiments, Impurity C is a process by-product or degradation product. In some embodiments, Impurity C is a degradation product. In some embodiments, the impurity is an Impurity C salt. In some embodiments, the impurity is an Impurity C methanesulfonate salt.

In some embodiments, the impurity is one or more of Impurity A, Impurity B, and Impurity C, or a salt thereof. In some embodiments, the salt is a methanesulfonic acid salt.

In some embodiments of the compounds of the invention, the impurity is an alcohol solvent. In some embodiments of the compounds of the invention, the alcohol solvent is methanol, ethanol, n-propanol, or isopropanol.

In some embodiments of the compounds of the invention, the impurity is toluene.

In some embodiments of the compounds of the invention, the impurity is acetone, ethyl acetate, or methyl t-butyl ether. In some embodiments, the impurity is water. In some embodiments of the compounds of the invention, the impurity is a solvent.

The present invention further provides a sealed container containing a compound of the invention and an inert gas. In some embodiments, the inert gas is argon or nitrogen.

The present invention further provides a sealed container containing the isolated phentolamine mesylate and an inert gas. In some embodiments, the inert gas is argon or nitrogen.

The present invention further provides a sealed container containing the filtered phentolamine mesylate and an inert gas. In some embodiments, the inert gas is argon or nitrogen.

The present invention further provides a sealed container containing the dried phentolamine mesylate and an inert gas. In some embodiments, the inert gas is argon or nitrogen.

Therapeutic Methods of the Invention

In some embodiments, the compound of the invention is useful for inhibiting the contraction of smooth muscle of the iris. Accordingly, the invention further provides methods for inhibiting the contraction of smooth muscle of the iris, comprising administering to a subject in need thereof an effective amount of the compound of the invention.

In some embodiments, the compound of the invention is useful for reducing pupil diameter. Accordingly, the invention further provides methods for reducing pupil diameter, comprising administering to a subject in need thereof an effective amount of the compound of the invention.

In some embodiments, the compound of the invention is useful for improving visual contrast sensitivity or visual acuity. Accordingly, the invention further provides methods for improving visual contrast sensitivity or visual acuity, comprising administering to a subject in need thereof an effective amount of the compound of the invention.

In some embodiments, the compound of the invention is useful for treating a dim or night vision disturbance. Accordingly, the invention further provides methods for treating a dim or night vision disturbance, comprising administering to a subject in need thereof an effective amount of the compound of the invention.

In some embodiments, the compound of the invention is useful for treating or reversing pharmacologically induced mydriasis. Accordingly, the invention further provides methods for treating or reversing pharmacologically induced mydriasis, comprising administering to a subject in need thereof an effective amount of the compound of the invention.

In some embodiments, the compound of the invention is useful for treating presbyopia. Accordingly, the invention further provides methods for treating presbyopia, comprising administering to a subject in need thereof an effective amount of the compound of the invention.

In some embodiments, the administering is topically instilling into a subject's eye.

In some embodiments, the effective amount of the compound of the invention is about 0.01 mg to about 100 mg. In some embodiments, the effective amount of the compound of the invention is about 0.05 mg to about 50 mg. In some embodiments, the effective amount of the compound of the invention is about 0.1 mg to about 100 mg. In some embodiments, the effective amount of the compound of the invention is about 1 mg to about 25 mg. In some embodiments, the effective amount of the compound of the invention is about 5 mg to about 10 mg.

In some embodiments, the effective amount of the compound of the invention is about 0.1 mg to about 2.0 mg, about 0.2 mg to about 0.7 mg, about 0.4 mg to about 0.6 mg, or about 0.8 mg to about 1.2 mg. In some embodiments, the effective amount of the compound of the invention is about 0.5 mg or about 1 mg.

In some embodiments, the effective amount of the compound of the invention is about 0.1 mg to about 2.0 mg. In some embodiments, the effective amount of the compound of the invention is about 0.1 mg to about 1.0 mg. In some embodiments, the effective amount of the compound of the invention is about 0.2 mg to about 0.7 mg. In some embodiments, the effective amount of the compound of the invention is about 0.4 mg to about 0.6 mg. In some embodiments, the effective amount of the compound of the invention is about 0.25 mg, about 0.5 mg or about 1.0 mg. In some embodiments, the effective amount of the compound of the invention is about 0.5 mg.

Pharmaceutical Compositions

In some embodiments, the compound of the invention is present in a composition. In some embodiments, the composition is a pharmaceutical composition. In some embodiments, the compositions comprise a compound of the invention and a pharmaceutically acceptable carrier or excipient.

In some embodiments, the compositions are formulated for administration by a variety of means including orally, parenterally, by inhalation spray, topically, or rectally. The term "parenteral" as used here includes subcutaneous, intravenous, intramuscular, and intraarterial injections with a variety of infusion techniques. Intraarterial and intravenous injection as used herein includes administration through catheters.

In some embodiments, the composition is a solution, a suspension, an emulsion, a tablet, a pill, a capsule, a powder, a cream, or a gel.

In some embodiments, the pharmaceutical composition is an ophthalmic solution. In some embodiments, the ophthalmic solution comprises a compound of the invention in about 0.5% to about 2% by weight of the ophthalmic solution. In some embodiments, the ophthalmic solution comprises a compound of the invention in an amount that is molar equivalent to about 0.5% to about 5% of Compound 1 by weight or volume of the ophthalmic solution. In some embodiments, the ophthalmic solution comprises a compound of the invention in an amount that is molar equivalent to about 0.35% or about 1% of Compound 1 by weight or volume of the ophthalmic solution. In some embodiments, the ophthalmic solution comprises a compound of the invention in an amount that is molar equivalent to about 0.37% or about 0.5% of Compound 1 by weight or volume of the ophthalmic solution. In some embodiments, the ophthalmic solution comprises a compound of the invention in an amount of about 0.35% or about 0.75% by weight or volume of the ophthalmic composition.

In some embodiments, the composition comprises about 1% of phentolamine mesylate by weight of the composition. In some embodiments, the composition comprises about 1% of phentolamine mesylate by volume of the composition. In some embodiments, the composition is an ophthalmic composition.

In some embodiments, the composition comprises about 0.5% of phentolamine mesylate by weight of the composition. In some embodiments, the composition comprises about 0.5% of phentolamine mesylate by volume of the composition. In some embodiments, the composition is an ophthalmic composition.

In some embodiments, the ophthalmic solution is suitable for ocular administration or ophthalmic use. In some embodiments, the ophthalmic solution is suitable for topical, subconjunctival, intravitreal, retrobulbar, intracameral or systemic administration.

In some embodiments, the pharmaceutically acceptable carrier or vehicle is a stabilizer, binder, filler, diluent, disintegrant, wetting agent, lubricant, glidant, coloring agent, dye-migration inhibitor, sweetening agent, flavoring agent, viscosity modifying agent, pH adjusting agent, buffer, osmotic agent, chelating agent, surfactants, or co-solvent.

In some embodiments, a viscosity modifying agent is polyvinyl alcohol, poloxamers, hyaluronic acid, carbomers, and polysaccharides, that is, cellulose derivatives, gellan gum, or xanthan gum.

In some embodiments, the pharmaceutically acceptable carrier or vehicle is sterile water, sterile buffer solution, or sterile saline.

In some embodiments, the pharmaceutically acceptable carrier or vehicle comprises or is mannitol or sodium acetate.

In some embodiments, the compositions of the invention comprise a preservative. In some embodiments, the preservative is benzalkonium chloride, cetrimide, polyquaternium-1, thimerosal, sodium perborate, stabilized oxychloro complex, stabilized chlorite peroxide, chlorhexidine, chlorobutanol, phenylethanol or methylparaben.

In some embodiments, the compositions of the invention do not comprise a preservative. In some embodiments, the compositions are preservative free.

In some embodiments, the compositions of the invention have a pH in the range of about 4 to about 6. In some embodiments, the compositions of the invention have a pH in the range of about 4.5 to about 5.3. In some embodiments, the compositions have a pH of about 4.5, about 4.6, about 4.7, about 4.8, about 4.9, about 5.0, about 5.1, about 5.2, or about 5.3.

In some embodiments, a composition of the invention is contained in a sealed container. In some embodiments, the sealed container further contains an inert gas. In some embodiments, the inert gas is argon or nitrogen.

In some embodiments, the compositions of the invention are useful for inhibiting the contraction of smooth muscle of the iris. Accordingly, the invention further provides methods for inhibiting the contraction of smooth muscle of the iris, comprising administering to a subject in need thereof an effective amount of a composition of the invention.

In some embodiments, the compositions of the invention are useful for reducing pupil diameter. Accordingly, the invention further provides methods for reducing pupil diameter, comprising administering to a subject in need thereof an effective amount of a composition of the invention.

In some embodiments, the compositions of the invention are useful for improving visual contrast sensitivity or visual acuity. Accordingly, the invention further provides methods for improving visual contrast sensitivity or visual acuity, comprising administering to a subject in need thereof an effective amount of a composition of the invention.

In some embodiments, the compositions of the invention are useful for treating a dim or night vision disturbance. Accordingly, the invention further provides methods for treating a dim or night vision disturbance, comprising administering to a subject in need thereof an effective amount of a composition of the invention.

In some embodiments, the compositions of the invention are useful for treating or reversing pharmacologically induced mydriasis. Accordingly, the invention further provides methods for treating or reversing pharmaceutically induced mydriasis, comprising administering to a subject in need thereof an effective amount of a composition of the invention.

In some embodiments, the compositions of the invention are useful for treating presbyopia. Accordingly, the invention further provides methods for treating presbyopia, comprising administering to a subject in need thereof an effective amount of a composition of the invention.

In some embodiments, the administering is topically instilling into the subject's eye.

EXAMPLES

Example 1. Synthesis of Phentolamine Mesylate from Compound 1

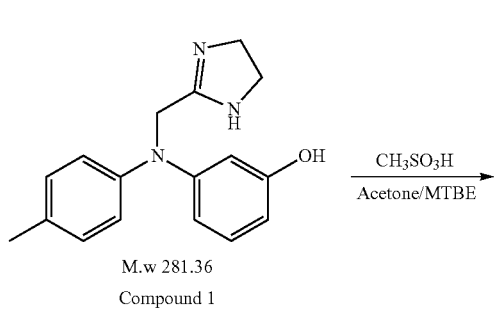

M.w 281.36
Compound 1

-continued

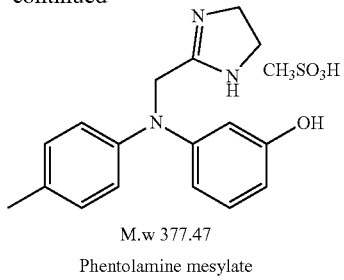

M.w 377.47

Phentolamine mesylate

To a suspension of 3-[[(4,5-dihydro-1H-imidazol-2-yl)methyl](4-methylphenyl)amino] phenol (Compound 1; 145 g, 515.35 mmol) in a mixture of acetone (1560 mL) and water (134 mL) was added methanesulfonic acid (54.5 g, 567 mmol, 1.1 equiv.) over 20 min under argon atmosphere. The temperature of reaction mixture spontaneously increased from 20° C. to 29.4° C. The reaction mixture became clear solution, and the reaction mixture was allowed to continue to stir at room temperature for 0.5 h. Methyl t-butyl ether (MTBE; 1450 mL) was added to the reaction mixture. The resultant mixture was cooled to 0±3° C. at a rate of about 1.33° C./minute for about 15 minutes. Phentolamine mesylate began to precipitate from the mixture when it reached a temperature of about 11° C. After reaching 0±3° C., the mixture was maintained at this temperature for 1 h, further cooled to −20±3° C. at a rate of about 1° C./minute for about twenty minutes and maintained at −20±3° C. for 3 h with stirring. The precipitate was collected by vacuum filtration, washed with MTBE (435 mL), dried using a 1-L rotavapor at 43° C. under reduced pressure (40 mbar) for 48 hours and further dried via lyophilization to provide 3-[[(4,5-dihydro-1H-imidazol-2-yl)methyl](4-methyl phenyl)amino]phenol mesylate (phentolamine mesylate; 171 g, yield: 87.9%) as a white solid. HPLC: 99.95%. $^1$H NMR (300 MHz, DMSO-$d_6$/TMS): δ 9.99 (s, 2H), 9.31 (s, 1H), 7.18 (d, J=8.1 Hz, 2H), 7.08 (d, J=8.1 Hz, 2H), 7.02 (t, J=8.1 Hz, 1H), 6.33 (dd, J=7.2 Hz, J=1.8 Hz, 1H), 6.24 (dd, J=7.2 Hz, J=1.8 Hz, 1H), 6.20 (s, 1H), 4.73 (s, 2H), 3.81 (s, 4H), 2.30 (s, 3H), 2.27 (s, 3H). $^{13}$C NMR (75 MHz, DMSO-$d_6$/TMS): δ 170.2, 158.6, 149.2, 144.5, 133.9, 130.5, 130.3, 124.3, 108.7, 108.6, 105.4, 49.3, 44.9, 20.8.

Example 2. Synthesis of Phentolamine Mesylate from Compound 1

To a suspension of 3-[[(4,5-dihydro-1H-imidazol-2-yl)methyl](4-methylphenyl)amino] phenol (Compound 1; 828 g, 2.91 mmol) in a mixture of acetone (8900 mL) and water (765 mL) was added methanesulfonic acid (311 g, 3.21 mol, 1.1 equiv.) over 30 minutes under argon atmosphere. The temperature of reaction mixture was spontaneously increased from 15.7° C. to 26° C. The reaction mixture became clear, and the reaction mixture was allowed to continue to stir at room temperature for 0.5 h. MTBE (8280 mL) was added to the above reaction mixture. The resultant mixture was cooled to 0±3° C. at a rate of about 1.33° C./minute for about 15 minutes. Phentolamine mesylate began to precipitate from the mixture when it reached a temperature of about 11° C. After reaching 0±3° C., the mixture was maintained at this temperature for 1 h, further cooled to −20±3° C. at a rate of about 1° C./minute for about twenty minutes and maintained at −20±3° C. for 3 h with stirring. The resultant precipitate was collected by vacuum filtration, washed with MTBE (1240 mL×2), dried using a 10-L rotavapor at 43° C. under reduced pressure (40 mbar) for 5 h and then at 6 mbar for 5 h to provide 3-[[(4,5-dihydro-1H-imidazol-2-yl)methyl](4-methyl phenyl)amino] phenol mesylate (phentolamine mesylate; 956.2 g, yield: 86.6%) as off-white solid. HPLC: 99.55%. $^1$H NMR (300 MHz, DMSO-$d_6$/TMS): δ 9.99 (s, 2H), 9.31 (s, 1H), 7.18 (d, J=8.1 Hz, 2H), 7.08 (d, J=8.1 Hz, 2H), 7.02 (t, J=8.1 Hz, 1H), 6.33 (dd, J=7.2 Hz, J=1.8 Hz, 1H), 6.24 (dd, J=7.2 Hz, J=1.8 Hz, 1H), 6.20 (s, 1H), 4.73 (s, 2H), 3.81 (s, 4H), 2.30 (s, 3H), 2.27 (s, 3H). $^{13}$C NMR (75 MHz, DMSO-$d_6$/TMS): δ 170.2, 158.6, 149.2, 144.5, 133.9, 130.5, 130.3, 124.3, 108.7, 108.6, 105.4, 49.3, 44.9, 20.8.

X-ray powder diffraction (XRPD) analysis was carried out using a Bruker D8 Discover diffractometer with DAVINCI configuration, in transmission mode (scan type: TwoTheta or Offset Coupled TwoTheta/Theta) scanning about 5 mg phentolamine mesylate obtained according to Example 2 at between 1.5 and 45° 2θ angles, and using the following measurements characteristics: acquisition time was 53 minutes, increment per step was 0.01°, time per step was 0.7 s, and generator voltage/generator amperage was 40 mA/40 kV to reach 1.6 kW power.

The raw data was imported in the Diffrac.EVA5.0 software and it was processed using the subsequent parameters: background subtraction and Kα2 stripping were performed before peak determination, and the peak search operation was performed with a threshold of 1 and a peak width of 0.153 for the sample. Only the resulting peaks having relative intensity greater than 2% were considered. The degree of crystallinity was calculated using the Diffrac.EVA5.0 software option. The degree of crystallinity of the phentolamine mesylate obtained according to Example 2 was 91.5% with 8.5% amorphous phase, indicating that the material has a high degree of crystallinity.

FIG. 1 shows an XRPD diffractogram of the phentolamine mesylate obtained as described in Example 2, and Table 1 lists XRPD peaks represented in FIG. 1.

TABLE 1

| Angle 2θ (°) | Net Intensity (counts) | Rel. Intensity (%) |
|---|---|---|
| 6.57 | 805.22 | 14.95 |
| 6.87 | 5206.82 | 96.67 |
| 8.42 | 893.45 | 16.59 |
| 8.53 | 901.65 | 16.74 |
| 8.91 | 532.10 | 9.88 |
| 10.11 | 117.23 | 2.18 |
| 10.91 | 133.62 | 2.48 |
| 11.17 | 308.59 | 5.73 |
| 11.65 | 1889.71 | 35.08 |
| 12.59 | 144.89 | 2.69 |
| 13.15 | 1821.07 | 33.81 |
| 14.71 | 1189.28 | 22.08 |
| 15.37 | 751.55 | 13.95 |
| 15.77 | 127.26 | 2.36 |
| 16.34 | 439.51 | 8.16 |
| 16.70 | 949.27 | 17.62 |
| 16.91 | 771.33 | 14.32 |
| 18.47 | 1068.87 | 19.84 |
| 18.86 | 3141.95 | 58.33 |
| 19.38 | 1238.07 | 22.99 |
| 20.05 | 1172.06 | 21.76 |
| 20.32 | 4672.35 | 86.74 |
| 20.85 | 2119.29 | 39.35 |
| 21.07 | 2173.39 | 40.35 |
| 21.36 | 5386.33 | 100.00 |
| 21.70 | 911.37 | 16.92 |
| 22.07 | 778.80 | 14.46 |
| 22.22 | 973.63 | 18.08 |
| 22.95 | 176.18 | 3.27 |

TABLE 1-continued

| Angle 2θ (°) | Net Intensity (counts) | Rel. Intensity (%) |
|---|---|---|
| 23.24 | 955.36 | 17.74 |
| 23.53 | 257.04 | 4.77 |
| 23.87 | 1368.83 | 25.41 |
| 24.50 | 480.43 | 8.92 |
| 24.65 | 333.87 | 6.20 |
| 25.51 | 290.85 | 5.40 |
| 26.11 | 193.68 | 3.60 |
| 26.36 | 338.79 | 6.29 |
| 27.09 | 592.24 | 11.00 |
| 27.42 | 368.10 | 6.83 |
| 27.63 | 728.26 | 13.52 |
| 27.90 | 269.32 | 5.00 |
| 28.50 | 164.20 | 3.05 |
| 28.98 | 124.03 | 2.30 |
| 29.43 | 321.41 | 5.97 |
| 29.91 | 191.28 | 3.55 |
| 30.43 | 209.46 | 3.89 |
| 31.24 | 196.52 | 3.65 |
| 31.56 | 122.73 | 2.28 |
| 31.91 | 437.68 | 8.13 |
| 32.10 | 347.49 | 6.45 |
| 32.31 | 436.38 | 8.10 |
| 32.53 | 423.20 | 7.86 |
| 33.14 | 218.06 | 4.05 |
| 33.26 | 216.37 | 4.02 |
| 35.14 | 436.48 | 8.10 |
| 36.33 | 182.53 | 3.39 |
| 37.57 | 109.35 | 2.03 |
| 37.89 | 209.42 | 3.89 |
| 38.43 | 113.71 | 2.11 |
| 39.61 | 111.10 | 2.06 |
| 40.36 | 193.23 | 3.59 |

Thermo-gravimetric (TG)/differential scanning calorimetric (DSC) analysis was carried out. A sample of phentolamine mesylate (about 9 mg) obtained according to Example 2 was weighed into an open aluminum pan, loaded into a simultaneous Setaram LABSYS EVO thermo-gravimetric/differential scanning calorimeter (TG-DTA/DSC) and maintained at 30° C. for 15 minutes. The sample was then heated from 30° C. to 550° C., during which time a change in sample weight was recorded along with any differential thermal events. Nitrogen was used as a purge gas, at a flow rate of 180 cm³/min. Prior to the analysis, the instrument mass loss and temperature were calibrated using copper sulfate pentahydrate and reference standards (lead and indium), respectively. The sample analysis was carried out with the help of CALISTO software, where the corresponding mass loss and temperatures of thermal events were quoted as the onset temperature, measured according to the manufacturer's specifications. The analysis was carried out with a heating rate of 10° C./minute and the background was subtracted before further processing.

The TG/DSC analysis showed 3 endothermic events (peak maxima at about 120° C., 133° C., and about 180° C.) and one exothermic event (FIG. 2).

The TG/DSC analysis did not show any thermic event that indicates or suggests that the sample lost water.

Example 3. Comparison of Powder XRPD Patterns and TG/DSC Thermograms

The XRPD analysis and TG/DSC analysis of commercially available United States Pharmacopeia (USP) reference standard phentolamine mesylate (purity: 99.5%) were carried out as described in Example 2. The XRPD pattern and the TG/DSC thermograms of the phentolamine mesylate USP reference standard were compared to those of the phentolamine mesylate obtained according to Example 2.

The degree of crystallinity of the phentolamine mesylate USP reference standard was 85.1% with 14.9% amorphous phase, compared to the phentolamine mesylate obtained according to Example 2, which has a degree of crystallinity of 91.5% with 8.5% amorphous phase.

FIG. 3 shows an XRPD diffractogram of the phentolamine mesylate USP reference standard, and Table 2 lists XRPD peaks represented in FIG. 3.

TABLE 2

| Angle 2θ (°) | Net Intensity (counts) | Rel. Intensity (%) |
|---|---|---|
| 6.67 | 287.05 | 6.10 |
| 6.92 | 656.31 | 13.95 |
| 8.26 | 113.50 | 2.41 |
| 8.57 | 380.56 | 8.09 |
| 10.17 | 128.57 | 2.73 |
| 11.22 | 258.56 | 5.50 |
| 11.71 | 1718.23 | 36.53 |
| 14.73 | 328.32 | 6.98 |
| 15.44 | 662.52 | 14.09 |
| 16.76 | 797.82 | 16.96 |
| 16.94 | 125.17 | 2.66 |
| 17.80 | 127.99 | 2.72 |
| 18.14 | 149.55 | 3.18 |
| 18.59 | 1108.99 | 23.58 |
| 18.94 | 1423.19 | 30.26 |
| 19.22 | 267.97 | 5.70 |
| 19.54 | 577.37 | 12.28 |
| 20.40 | 4703.14 | 100.00 |
| 20.66 | 373.47 | 7.94 |
| 21.15 | 1970.68 | 41.90 |
| 21.42 | 3983.23 | 84.69 |
| 21.76 | 877.82 | 18.66 |
| 22.14 | 575.15 | 12.23 |
| 22.33 | 148.16 | 3.15 |
| 22.91 | 124.08 | 2.64 |
| 23.33 | 750.03 | 15.95 |
| 23.93 | 1355.51 | 28.82 |
| 24.58 | 488.33 | 10.38 |
| 24.70 | 303.72 | 6.46 |
| 26.15 | 225.95 | 4.80 |
| 26.53 | 163.51 | 3.48 |
| 27.19 | 185.76 | 3.95 |
| 27.69 | 797.21 | 16.95 |
| 27.99 | 224.00 | 4.76 |
| 29.07 | 126.74 | 2.69 |
| 29.57 | 195.09 | 4.15 |
| 31.27 | 167.71 | 3.57 |
| 31.99 | 228.62 | 4.86 |
| 32.39 | 331.96 | 7.06 |
| 32.64 | 259.17 | 5.51 |
| 33.23 | 140.20 | 2.98 |
| 33.41 | 210.77 | 4.48 |
| 34.31 | 97.99 | 2.08 |
| 37.97 | 102.05 | 2.17 |
| 38.53 | 94.74 | 2.01 |
| 40.43 | 196.96 | 4.19 |

Table 3 lists selected peaks of the XRPD pattern of the phentolamine mesylate obtained according to Example 2.

TABLE 3

| Angle 2θ (°) | Net Intensity (counts) | Rel. Intensity (%) |
|---|---|---|
| 8.91 | 532.1 | 9.88 |
| 10.91 | 133.62 | 2.48 |
| 12.59 | 144.89 | 2.69 |
| 13.15 | 1821.07 | 33.81 |
| 16.34 | 439.51 | 8.16 |
| 25.51 | 290.85 | 5.4 |
| 28.50 | 164.2 | 3.05 |
| 29.91 | 191.28 | 3.55 |
| 30.43 | 209.46 | 3.89 |

TABLE 3-continued

| Angle 2θ (°) | Net Intensity (counts) | Rel. Intensity (%) |
|---|---|---|
| 31.56 | 122.73 | 2.28 |
| 35.14 | 436.48 | 8.1 |
| 36.33 | 182.53 | 3.39 |

The TG/DSC analysis showed one endothermic event (peak maximum at about 183° C.) and one exothermic event (FIG. 4).

Based on the TG/DSC data, both phentolamine mesylate obtained according to Example 2 and the phentolamine mesylate USP reference standard are anhydrous.

What is claimed is:

1. A method for making phentolamine mesylate, comprising:
    (a) allowing Compound 1

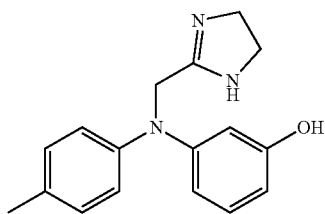

1 to react with methanesulfonic acid in the presence of acetone and water under conditions effective to make a first mixture comprising phentolamine mesylate;
    (b) admixing the first mixture and methyl t-butyl ether to make a second mixture; and
    (c) allowing the phentolamine mesylate to precipitate from the second mixture.

2. The method of claim 1, wherein allowing the phentolamine mesylate to precipitate from the second mixture comprises cooling the second mixture to a temperature of 15° C. to −25° C.

3. The method of claim 1, further comprising the step of:
    (d) isolating the phentolamine mesylate from the second mixture, wherein the isolating provides isolated phentolamine mesylate.

4. The method of claim 3, wherein the isolating is filtering, and the isolated phentolamine mesylate is filtered phentolamine mesylate.

5. The method of claim 3, further comprising the step of:
    (e) drying the isolated phentolamine mesylate to provide dried phentolamine mesylate.

6. The method of claim 1, wherein the acetone and water are present in the first mixture of step (a) in a ratio of 10 (plus or minus up to 20%):1 acetone:water by volume to 12 (plus or minus up to 20%):1 acetone:water by volume.

7. The method of claim 1, wherein Compound 1 is present in the first mixture of step (a) at a concentration of 0.2 (plus or minus up to 20%) moles/liter of the acetone and water to 0.4 (plus or minus up to 20%) moles/liter of the acetone and water.

8. The method of claim 5, wherein the dried phentolamine mesylate has purity of at least 98% by weight of the dried phentolamine mesylate.

9. The method of claim 5, wherein the dried phentolamine mesylate has a purity of 99.0% to 100% by weight of the dried phentolamine mesylate.

10. The method of claim 5, wherein the dried phentolamine mesylate comprises less than 0.5% of an impurity by weight of the dried phentolamine mesylate.

11. The method of claim 5, wherein the dried phentolamine mesylate is not subject to further purification.

12. Phentolamine mesylate that exhibits an X-ray powder diffraction (XRPD) pattern comprising a peak at 6.87±0.2 degrees 2-theta, a peak at 20.32±0.2 degrees 2-theta, and a peak at 21.36±0.2 degrees 2-theta.

13. The phentolamine mesylate of claim 12, wherein the XRPD pattern further comprises a peak at 18.86±0.2 degrees 2-theta and a peak at 21.07±0.2 degrees 2-theta.

14. The phentolamine mesylate of claim 13, wherein the XRPD pattern further comprises a peak at 11.65±0.2 degrees 2-theta, at 13.15±0.2 degrees 2-theta, and a peak at 20.85±0.2 degrees 2-theta.

15. The phentolamine mesylate of claim 12, wherein the phentolamine mesylate comprises less than 1% of an impurity by weight of the phentolamine mesylate.

16. The phentolamine mesylate of claim 12 having a molar ratio of crystalline phentolamine mesylate to amorphous phentolamine mesylate of at least 9:1.

17. A composition comprising an effective amount of the phentolamine mesylate of claim 12 and a pharmaceutically acceptable carrier or excipient.

18. The composition of claim 17, wherein the composition is an ophthalmic solution.

19. The composition of claim 17, wherein the composition comprises the phentolamine mesylate in an amount of 1% by weight or volume of the composition.

20. A method for a) inhibiting contraction of smooth muscle of a subject's iris, b) reducing a subject's pupil diameter, or c) improving visual contrast sensitivity or visual acuity, comprising administering to a subject in need of a) inhibition of iris smooth muscle contraction, b) reduction of pupil diameter or c) improvement of visual contrast sensitivity or improvement of visual acuity, an effective amount of the phentolamine mesylate of claim 12.

21. A method for a) treating a dim or night vision disturbance, b) treating or reversing pharmacologically induced mydriasis, or c) treating presbyopia, comprising administering to a subject in need of a) treatment of dim or night vision disturbance, b) treatment or reversal of pharmacologically induced mydriasis or c) treatment of presbyopia, an effective amount of the phentolamine mesylate of claim 12.

* * * * *

UNITED STATES PATENT AND TRADEMARK OFFICE
CERTIFICATE OF CORRECTION

PATENT NO.         : 11,566,005 B2
APPLICATION NO.    : 17/747656
DATED              : January 31, 2023
INVENTOR(S)        : Daniela Carmen Oniciu It is certified that error appears in the above-identified patent and that said Letters Patent is hereby corrected as shown below:

In the Specification

Column 2, Line 52:
"late United States Pharmacopeia (USP) reference standard."
Should read:
-- late (Industriale Chimica, Saronno (VA), Italy) reference standard. --

Column 2, Lines 54-55:
"phentolamine mesylate USP reference standard and a DSC
thermogram of phentolamine mesylate USP reference stan-"
Should read:
-- phentolamine mesylate (Industriale Chimica, Saronno (VA), Italy) reference standard
and a DSC thermogram of the phentolamine mesylate reference stan- --

Column 33, Line 62:
"cially available United States Pharmacopeia (USP) refer-"
Should read:
-- cially available (Industriale Chimica, Saronno (VA), Italy) refer- --

Column 33, Line 66:
"USP reference standard were compared to those of the"
Should read:
-- reference standard were compared to those of the --

Column 34, Line 2:
"USP reference standard was 85.1 % with 14.9 % amorphous"
Should read:
-- reference standard was 85.1 % with 14.9 % amorphous --

Signed and Sealed this
Thirteenth Day of February, 2024

Katherine Kelly Vidal
*Director of the United States Patent and Trademark Office*

Column 34, Line 7:
"mesylate USP reference standard, and Table 2 lists XRPD"
Should read:
-- mesylate reference standard, and Table 2 lists XRPD --

Column 35, Line 14:
"mesylate USP reference standard are anhydrous."
Should read:
-- mesylate reference standard are anhydrous. --